(12) United States Patent
Shobayashi

(10) Patent No.: US 11,744,721 B2
(45) Date of Patent: Sep. 5, 2023

(54) HIGHLY FLEXIBLE STENT

(71) Applicant: BIOMEDICAL SOLUTIONS INC., Tokyo (JP)

(72) Inventor: Yasuhiro Shobayashi, Tokyo (JP)

(73) Assignee: Otsuka Medical Devices Co., Ltd., Tokyo (JP)

( * ) Notice: Subject to any disclaimer, the term of this patent is extended or adjusted under 35 U.S.C. 154(b) by 184 days.

(21) Appl. No.: 16/548,391

(22) Filed: Aug. 22, 2019

(65) Prior Publication Data

US 2019/0374357 A1 Dec. 12, 2019

Related U.S. Application Data

(63) Continuation of application No. 15/433,526, filed on Feb. 15, 2017, now abandoned, which is a
(Continued)

(30) Foreign Application Priority Data

Feb. 19, 2014 (JP) .................................. 2014-029933
Aug. 14, 2014 (JP) .................................. 2014-165104

(51) Int. Cl.
  *A61F 2/92* (2013.01)
  *A61F 2/915* (2013.01)
  (Continued)

(52) U.S. Cl.
  CPC ................ *A61F 2/92* (2013.01); *A61F 2/915* (2013.01); *A61F 2/966* (2013.01); *A61F 2/95* (2013.01);
  (Continued)

(58) Field of Classification Search
  CPC .... A61F 2/92; A61F 2/915; A61F 2/95; A61F 2/966
  See application file for complete search history.

(56) References Cited

U.S. PATENT DOCUMENTS 5,810,872 A   9/1998  Kanesaka et al.
5,948,016 A   9/1999  Jang
(Continued)

FOREIGN PATENT DOCUMENTS

CA   2 698 294 A1   2/2009
CA   2 759 441 A1   10/2010
(Continued)

OTHER PUBLICATIONS

Office Action dated Dec. 12, 2019 in corresponding KR Application No. KR10-2017-7017706, 4 pages.
(Continued)

*Primary Examiner* — Christopher D. Prone
(74) *Attorney, Agent, or Firm* — Muncy, Geissler, Olds & Lowe, P.C.

(57) ABSTRACT

A stent includes wavy-line pattern bodies having a wavy-line pattern and arranged side-by-side in an axial direction LD, and coiled elements arranged between the wavy-line pattern bodies adjacent and extending in a spiral manner around an axis. All apices on opposite sides of the wavy-line pattern of the wavy-line pattern bodies that are adjacent are connected by way of the coiled element. When viewing in a radial direction RD, a circular direction CD of the wavy-line pattern bodies is inclined with respect to the radial direction RD, and a winding direction of one of the coiled elements located at one side in the axial direction LD with respect to the wavy-line pattern bodies and a winding direction of one other of the coiled elements located at the other side in the axial direction LD are opposite.

2 Claims, 38 Drawing Sheets

Related U.S. Application Data continuation of application No. 14/408,203, filed as application No. PCT/JP2014/071469 on Aug. 15, 2014, now Pat. No. 9,603,733.

(51) Int. Cl.
*A61F 2/966* (2013.01)
*A61F 2/95* (2013.01)

(52) U.S. Cl.
CPC .................. *A61F 2002/9155* (2013.01); *A61F 2002/91575* (2013.01); *A61F 2230/0006* (2013.01); *A61F 2230/0023* (2013.01); *A61F 2230/0054* (2013.01); *A61F 2230/0069* (2013.01); *A61F 2230/0091* (2013.01)

(56) References Cited

U.S. PATENT DOCUMENTS

| | | | |
|---|---|---|---|
| 6,042,597 A | 3/2000 | Kveen et al. | |
| 6,641,590 B1 | 11/2003 | Palmer et al. | |
| 6,989,024 B2 * | 1/2006 | Hebert | A61F 2/95 623/1.11 |
| 8,801,772 B2 | 8/2014 | Shobayashi et al. | |
| 9,144,508 B2 | 9/2015 | Hebert et al. | |
| 2002/0022876 A1 | 2/2002 | Richter et al. | |
| 2005/0228472 A1 | 10/2005 | Case et al. | |
| 2009/0005856 A1 | 1/2009 | Pappas et al. | |
| 2009/0024205 A1 * | 1/2009 | Hebert | A61F 2/915 623/1.16 |
| 2009/0036976 A1 * | 2/2009 | Beach | A61F 2/915 623/1.22 |
| 2010/0010620 A1 | 1/2010 | Weber | |
| 2011/0106237 A1 | 5/2011 | Bonsignore et al. | |
| 2011/0230957 A1 | 9/2011 | Bonsignore | |
| 2011/0245910 A1 | 10/2011 | Beach et al. | |
| 2012/0035705 A1 | 2/2012 | Giasolli et al. | |
| 2012/0041540 A1 | 2/2012 | Shobayashi et al. | |
| 2012/0245671 A1 * | 9/2012 | Wainwright | A61B 17/12031 623/1.11 |
| 2013/0079869 A1 | 3/2013 | Straubinger et al. | |
| 2013/0268055 A1 | 10/2013 | Cottone | |

FOREIGN PATENT DOCUMENTS

| | | |
|---|---|---|
| EP | 2 394 610 A1 | 12/2011 |
| JP | H10-258125 A | 9/1998 |
| JP | H11-501551 A | 2/1999 |
| JP | 2005-500138 A | 1/2005 |
| JP | 2007-518516 A | 7/2007 |
| JP | 2008-544765 A | 12/2008 |
| JP | 2010-535075 A | 11/2010 |
| JP | 2011-512922 A | 4/2011 |
| RU | 2 169 545 C2 | 6/2001 |
| WO | WO 96/003092 A1 | 2/1996 |
| WO | WO 96/033671 A1 | 10/1996 |
| WO | WO 98/048733 A1 | 11/1998 |
| WO | WO-03/018085 A2 | 3/2003 |
| WO | WO-2005/072645 A1 | 8/2005 |
| WO | WO 2006/108010 A2 | 10/2006 |
| WO | WO2009/012417 A1 | 1/2009 |
| WO | WO 2009/012417 A1 | 1/2009 |
| WO | WO2009/017827 A1 | 2/2009 |
| WO | WO 2009/017827 A1 | 2/2009 |
| WO | WO 2010/090348 A1 | 8/2010 |
| WO | WO 2011/056981 A2 | 5/2011 |

OTHER PUBLICATIONS

Notice of Reasons for Rejection, dated Nov. 26, 2014 in corresponding JP Application 2014-165104, and an English translation thereof.
Extended European search report for European Patent Application No. 14772263.1 dated Sep. 30, 2016; pp. 1-7.
Notification of Reasons for Refusal dated Jun. 5, 2018 in JP Application No. 2015-020312.
Notification of Reasons for Refusal issued in the JP Patent Application No. JP2019-019519, dated Jun. 9, 2020.
Office Action issued in the KR Patent Application No. KR10-2017-7017706, dated Jun. 22, 2020.
Search Report and Written Opinion issued in corresponding SG application No. 10201705470Y dated Dec. 1, 2020 (10 pages).

* cited by examiner

FIG. 14
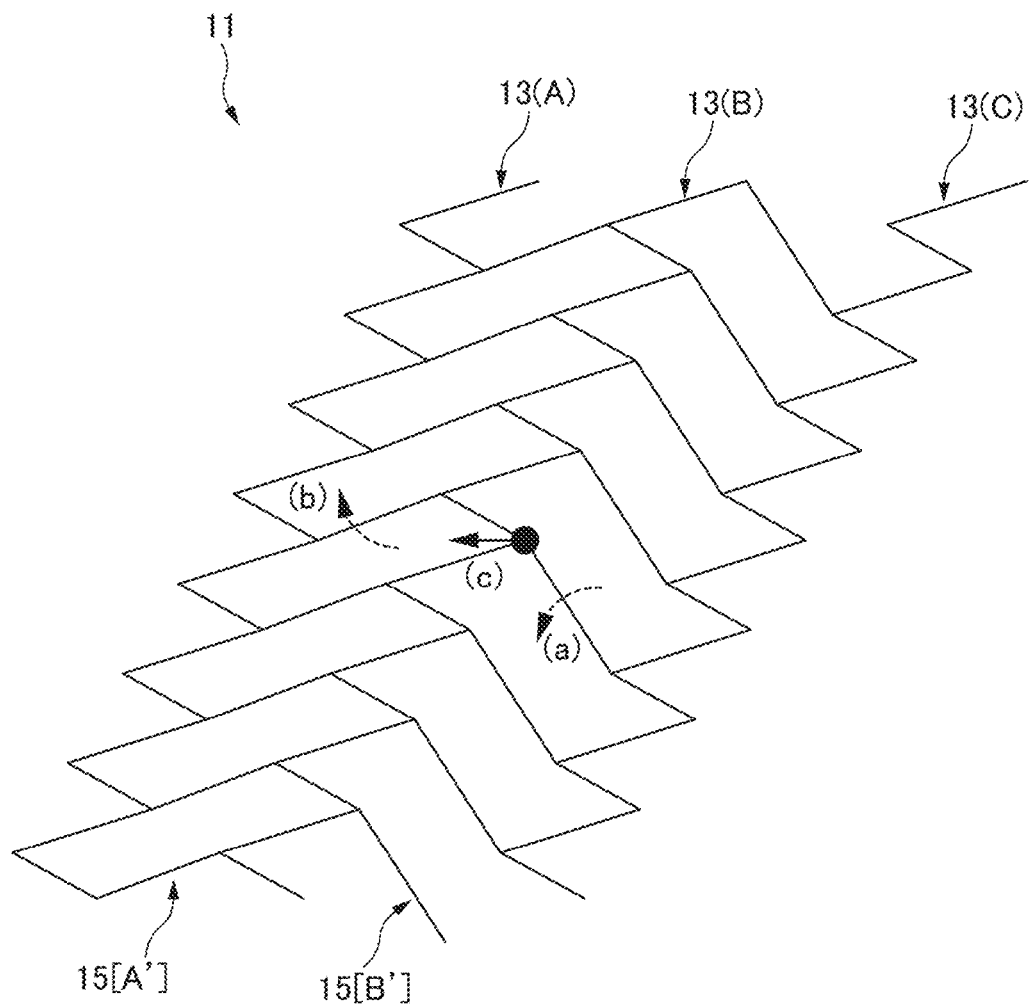
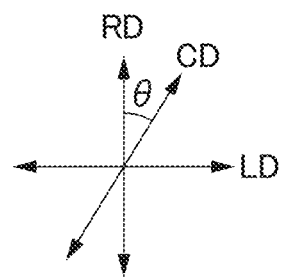

FIG. 16
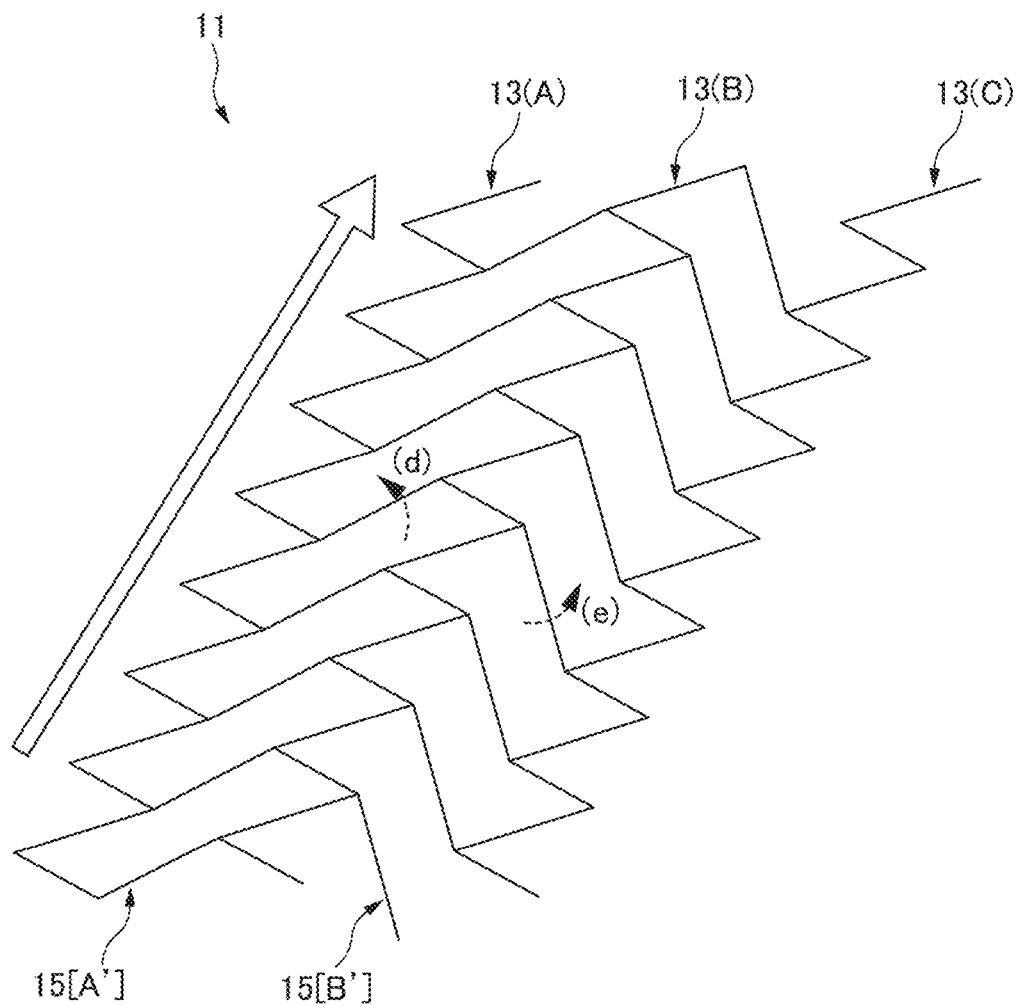
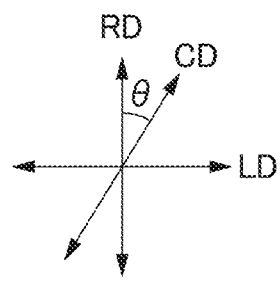

FIG. 17
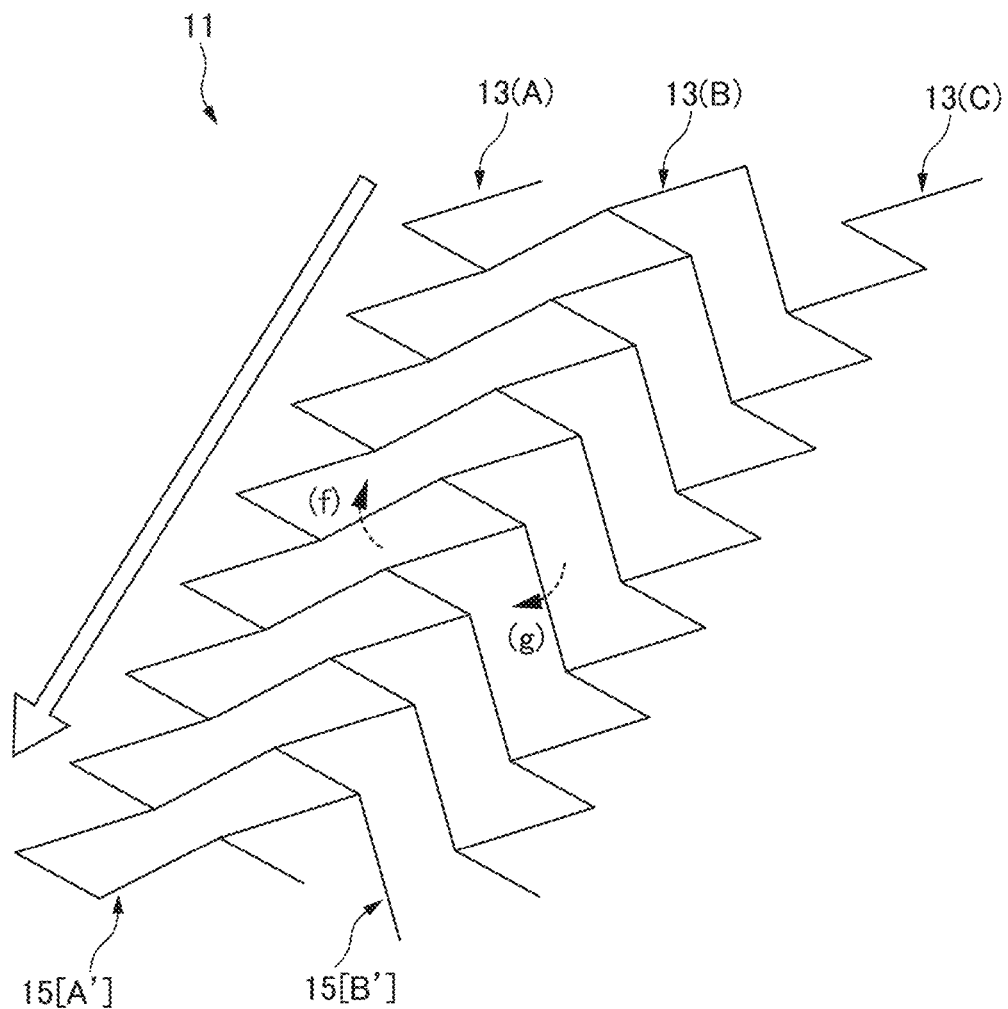
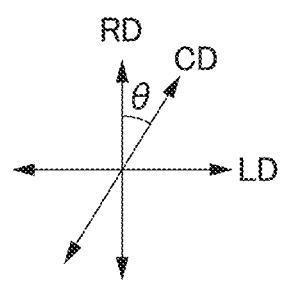

HIGHLY FLEXIBLE STENT

CROSS-REFERENCE TO RELATED APPLICATIONS

This application is a Continuation of co-pending application Ser. No. 15/433,526, filed on Feb. 15, 2017, which is a Continuation of application Ser. No. 14/408,203, filed on Dec. 15, 2014, and which has issued as U.S. Pat. No. 9,603,733 B2 on Mar. 28, 2017, which is a U.S. National Stage of International Application No. PCT/JP2014/071469 filed on Aug. 15, 2014, for which priority is claimed under 35 U.S.C. § 120; and this application claims priority of Application No. 2014-029933 filed in Japan on Feb. 19, 2014 and Application No. 2014/165104 filed in Japan on Aug. 154, 2014 under 35 U.S.C. § 119; the entire contents of all of which are hereby incorporated by reference.

TECHNICAL FIELD

The present invention relates to a highly flexible stent placed in a luminal structure of a living body in order to expand lumen.

BACKGROUND ART

In a biological organ having a luminal structure such as blood vessels, the trachea and the intestines, when stenosis occurs therein, a cylinder-shaped stent with mesh pattern is used in order to secure patency at a site of pathology by expanding an inner cavity at a narrowed part. These biological organs often have bent or tapered structures locally (i.e. a tubular structure of which sectional diameters of the inner cavity differ locally in an axial direction). Therefore, a stent having higher conformability has been desired which can flexibly adapt to such a complex vessel structure. Furthermore, in recent years, stents have come to also be employed for the treatment of cerebral blood vessels. Among tubular organs in a living body, the cerebral vessel system has a more complex structure. The cerebral vessel system has many bent sites and sites having tapered structures. Therefore, stents with particularly higher conformability have been required therein.

For the purpose of realizing a stent with higher conformability, the two kinds of mechanical flexibilities of a longitudinal axis direction (in a central axis direction) and a radial direction (a direction perpendicular to the longitudinal direction) of the stent are said to be important. Thereamong, the flexibility in a longitudinal axis direction refers to stiffness with respect to bending along a longitudinal axis direction or the ease of bending. The flexibility in a radial direction refers to stiffness with respect to expansion and contraction along a direction perpendicular to a longitudinal axis direction or the ease of expansion and contraction. The mechanical flexibility in a longitudinal axis direction is a property that is necessary for a stent to be flexibly bent along a longitudinal axis direction to allow adapting to a bent site of a tubular organ in a body. The mechanical flexibility in a radial direction is a property that is necessary for making the radius of a stent flexibly differ following the shape of an outer wall of a luminal structure of a tubular organ in a body so that the stent is in tight contact with the outer wall of the luminal structure. More specifically, regarding the latter, the flexibility in the radial direction, with consideration of not only a stent having lower stiffness, but also the stent being placed in an organ in a body having a tapered structure, it is necessary for a stent to have a property whereby the expansive force of the stent does not change greatly depending on local changes in sectional diameters of the inner cavity at a site having a tapered structure.

The structures of a stent are generally classified into the two types of open cell structures and closed cell structures. Since a stent having an open cell structure exerts remarkable mechanical flexibility in the longitudinal axis direction, the conformability is high and thus the open cell structures have been recognized as being effective for a stent structure that is placed in a tortuous tubular organ. However, for such an open cell structure, since a part of a strut of the stent may protrude radially outward in a flared shape when bent, there is a risk of damaging the tissue of a tubular organ in a body such as blood vessels when the stent is placed therein. On the other hand, regarding stents having a closed cell structure, there are those having closed cell structures that allow for a partial repositioning of a stent during operation, which had been difficult with stents of open cell structures, and stents having closed cell structures that allow for full repositioning of the stent during operation.

For such a closed cell structure, although there is no risk of the strut of the stent protruding radially outward such as a stent having an open cell structure, the flexibility of the structure tends to be lacking. Therefore, there has been a risk of inhibiting the flow of liquid such as blood in tubular organs from flowing due to a stent buckling when applying the stent having a closed cell structure to a bent tubular organ. Furthermore, structurally speaking, since the stent having a closed cell structure is inferior to the stent having an open cell structure in terms of a reduction in diameter, the stent having a closed cell structure cannot handle placement of a stent into a tubular organ of small diameter of around 2 mm, a result of which there has been a risk of damaging a body tissue.

In order to solve such problems, a spiral stent has been devised as a technology exhibiting high flexibility while being a stent having a closed cell structure (for example, refer to Japanese Unexamined Patent Application (Translation of PCT Publication), Publication No. 2010-535075.) The stent disclosed in Japanese Unexamined Patent Application (Translation of PCT Publication), Publication No. 2010-535075 includes spiral circular bodies having a wavy-line pattern and coiled elements connecting adjacent circular bodies in an expanded state.

Patent Document 1: Japanese Unexamined Patent Application (Translation of PCT Publication), Publication No. 2010-535075

DISCLOSURE OF THE INVENTION

Problems to be Solved by the Invention

However, after a stent has been placed in a superficial femoral artery, for example, inner and outer rotational actions of a femoral area cause inner and outer rotations of a blood vessel. The stent in the blood vessel thereby is also distorted in an inner rotational direction and an outer rotational direction. However, in Japanese Unexamined Patent Application (Translation of PCT Publication), Publication No. 2010-535075, since the deformed form of a stent differs depending on a direction in which the stent is distorted, distorted deformations of the stent due to the inner and outer rotations of the blood vessel become uneven, for example. Therefore, a difference arises in load on blood vessel walls from stents between left and right blood vessels. In particular, since there are differences among individuals in ratios of inner and outer rotations between left and right legs, for a patient who frequently performs an inner rotation of both legs, for example, in a case in which the stent is a stent that follows an inner rotation of the right leg, the stent cannot follow the inner rotation of the left leg. For this reason, since the load on the blood vessel walls from the stent differs between the left and right legs, even if treatment is done with the same stent, the rate of incurring a complicating disease after the stent being placed differs between the left and right legs.

Furthermore, since there are both inner and outer rotations for one leg, for example, the right leg, as described above, a stent that follows an inner rotation well cannot follow an outer rotation well. Due to the abovementioned problem, the following clinical problems occur:

(1) the risk of the stent being broken increases due to repetitive distorting loading; and (2) the risk of a blood vessel wall being damaged increases due to stress being applied intensively from a stent at a local portion thereof.

Regarding the stent of Japanese Unexamined Patent Application (Translation of PCT Publication), Publication No. 2010-535075, the coiled elements can be assumed approximately as a portion of the structure of a wound spring. Furthermore, if distorting loading is applied to the stent, deformation is caused intensively at the coiled elements. For this reason, it is possible to predict a reaction of a distorted deformation of this stent by considering of the distorted deformation of the spring structure of the coiled elements.

Here, distorted deformation behaviors in a case of assuming a deformation of a coiled element in an expanded state of the stent of Japanese Unexamined Patent Application (Translation of PCT Publication), Publication No. 2010-535075 as a part of a left-hand spring structure are illustrated in FIGS. 18B, 18C, 18E, and 18F. As illustrated in FIGS. 18B and 18E, when a distortion in a left-hand direction is applied to a left-hand spring, a force acts so as to be pulled in a perpendicular direction with respect to a cross section of an element wire of the spring. For this reason, as illustrated in FIGS. 18C and 18F, the element wire is deformed so as to be wound in the circumferential direction thereof and exhibits a behavior of being radially reduced in the radial direction. On the other hand, when a distortion in a right-hand direction is applied, a force acts so as to be compressed in a perpendicular direction with respect to the cross section of the element wire of the spring. For this reason, as illustrated in FIGS. 18A and 18D, the element wire is deformed so as to be pulled away in the circumferential direction thereof and exhibits a behavior of the outside diameter being expanded in a radial direction as a result.

Since the stent of Japanese Unexamined Patent Application (Translation of PCT Publication), Publication No. 2010-535075 is composed of a spring body, when distortion in a left or right direction is applied, it exhibits a behavior similar to the abovementioned distorted deformation of the wound spring. Due to this distorted deformation behavior, a substantial difference in deformation amounts in the radial direction of the stent between the distorted deformations in the left and right direction appears, whereby the load to blood vessel walls differs. Therefore, even when performing treatment with the same stent as describe above, treatment results may differ depending on target sites for treatment or difference among individuals.

Therefore, it is an object of the present invention to provide a highly flexible stent that can suppress a deformation amount in the radial direction of the stent with respect to a distortion load.

Means for Solving the Problems

The present invention relates to a highly flexible stent including: a plurality of wavy-line pattern bodies having a wavy-line pattern and arranged side-by-side in an axial direction; and a plurality of coiled elements arranged between the wavy-line pattern bodies that are adjacent and extending in a spiral manner around an axis, in which all apices on opposite sides of the wavy-line pattern of the wavy-line pattern bodies that are adjacent are connected by way of the coiled elements, in which, when viewing in a radial direction perpendicular to the axial direction, a circular direction of the wavy-line pattern bodies is inclined with respect to the radial direction, and in which a winding direction of one of the coiled elements located at one side in the axial direction with respect to the wavy-line pattern bodies and a winding direction of one other of the coiled elements located at the other side in the axial direction are opposite.

An angle at which the circular direction of the wavy-line pattern bodies inclines with respect to the radial direction may be 30° to 60°.

The wavy-line pattern bodies may form a circular body by connecting, in a circumferential direction, a plurality of waveform elements of substantially V-shape made by coupling two leg portions at an apex, and the length of the one of the coiled elements may be longer than the length of the leg portion and the length of the one other of the coiled elements may be shorter than the length of the leg portion.

The length of the one of the coiled elements may be no more than 1.5 times the length of the leg portion.

The wavy-line pattern bodies may be non-continuous in a circumferential direction and may not form a circular body, and may have a shape in which one or a plurality of struts that constitutes the wavy-line pattern bodies is omitted, as compared with the wavy-line pattern bodies that form a circular body.

A cross sectional shape may be a substantially triangular shape.

Effects of the Invention

According to the present invention, it is possible to provide a highly flexible stent that can suppress a deformation amount in the radial direction of the stent with respect to a distortion load.

BRIEF DESCRIPTION OF THE DRAWINGS

FIG. 14 is a schematic view showing the behavior of a coiled element and the center of the figure when the stent shown in FIG. 13 is bent;

FIG. 16 is a schematic view showing the behavior in a case in which a distortion in a right-hand direction is applied to the stent shown in FIG. 13;

FIG. 17 is a schematic view showing the behavior in a case in which a distortion in a left-hand direction is applied to the stent shown in FIG. 13;

Figure 1:
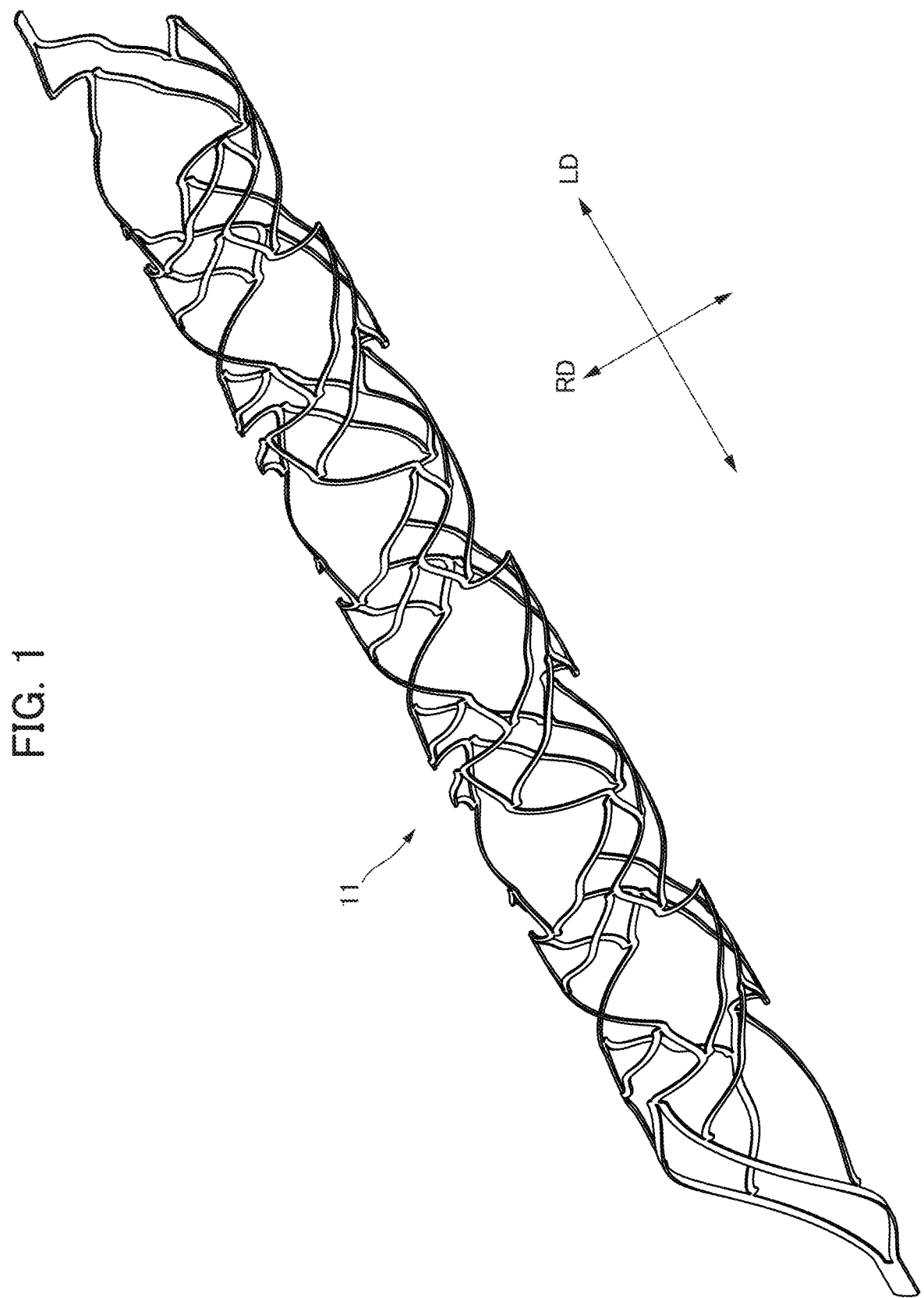
FIG. 1 is a perspective view showing a highly flexible stent in an unloaded state according to a first embodiment of the present invention.

EXPLANATION OF REFERENCE NUMERALS 11, 11A, 11B, 11C, 11D, 11E, 11F stent (highly flexible stent)
13 circular body (wavy-line pattern body)
15 coiled element
15L other coiled element
15R one coiled element
17 waveform element
17a leg portion
17b apex
19 knob portion
21 slit
LD axial direction (longitudinal axis direction)

RD radial direction
CD circular direction
θ angle inclined

PREFERRED MODE FOR CARRYING OUT THE INVENTION

Figure 2:
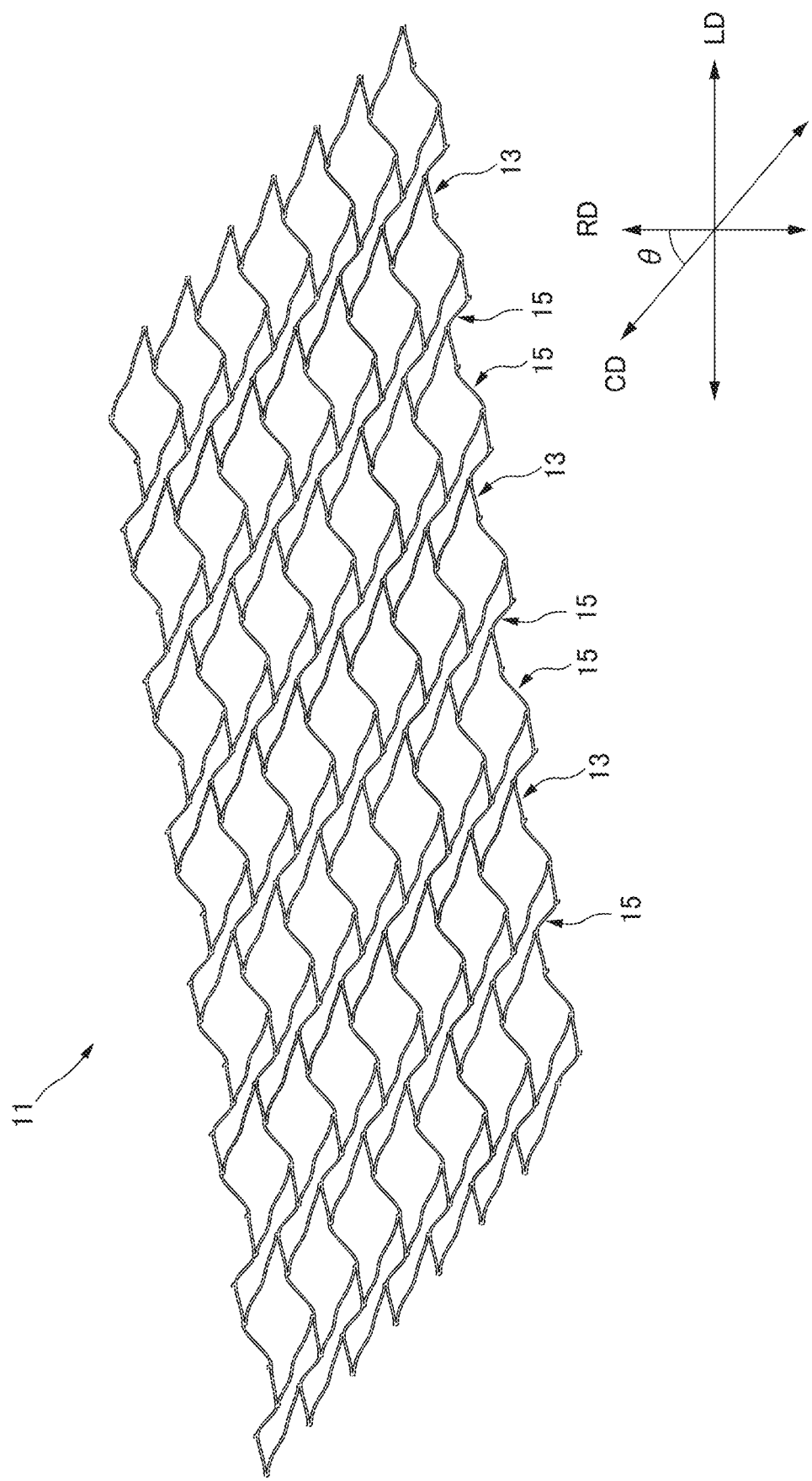
FIG. 2 is a developed view showing a highly flexible stent in an unloaded state according to a first embodiment of the present invention that is virtually expanded into a plane.
Figure 3:
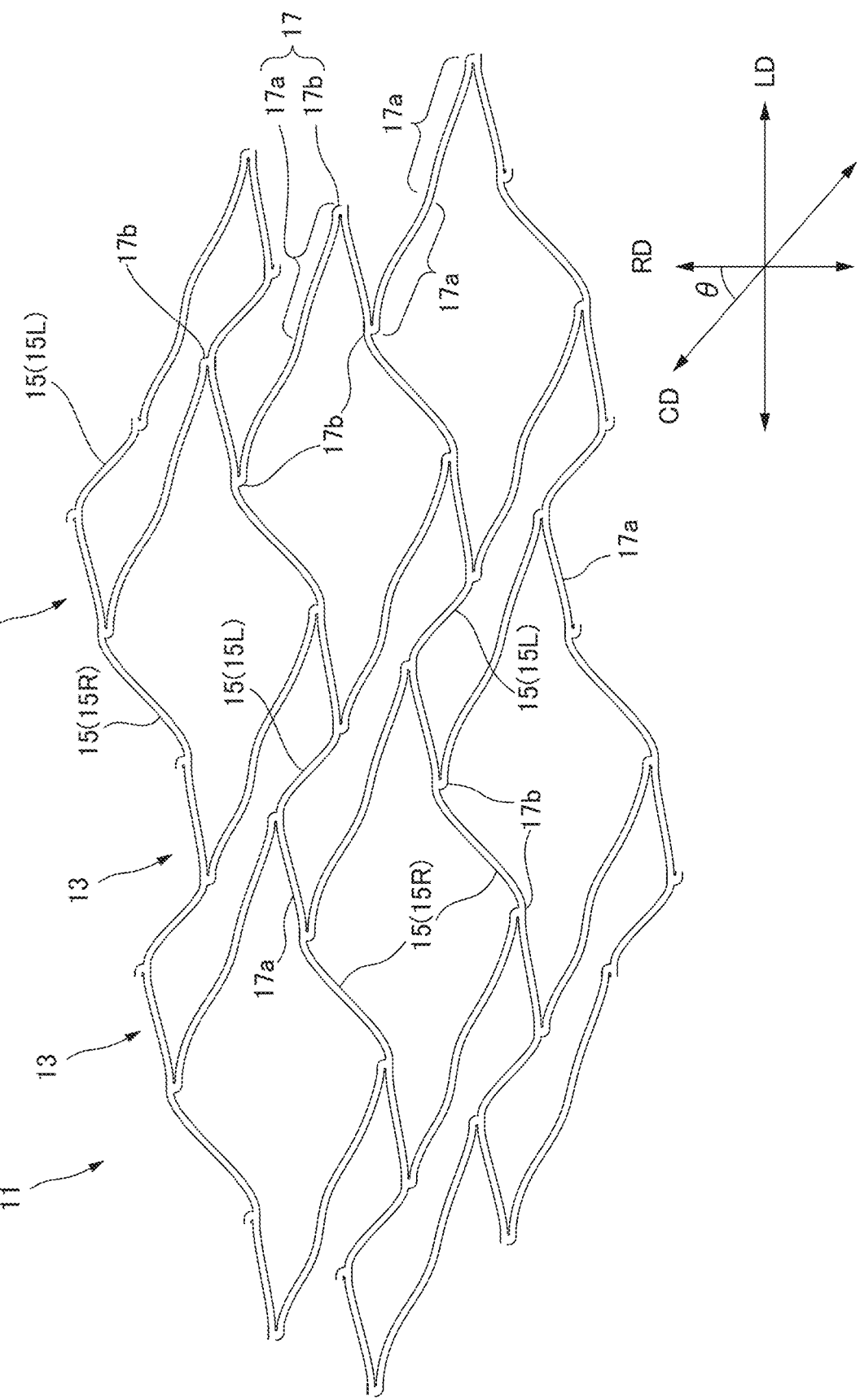
FIG. 3 is a partially enlarged view of the stent shown in FIG. 2.

In the following, a first embodiment of a highly flexible stent according to the present invention is described with reference to the drawings. With reference to FIGS. 1 to 3, first, the overall configuration of a highly flexible stent 11 according to the first embodiment of the present invention is described. FIG. 1 is a perspective view of a highly flexible stent according to the first embodiment of the present invention in an unloaded state. FIG. 2 is a developed view showing the highly flexible stent according to the first embodiment of the present invention in an unloaded state to be virtually expanded into a plane. FIG. 3 is a partially enlarged view of the stent shown in FIG. 2.

As illustrated in detail in FIG. 1, the stent 11 is of a substantially cylindrical shape. A peripheral wall of the stent 11 has a structure of a mesh pattern in which a plurality of closed cells having a congruent shape surrounded by wire-shaped materials is covering a circumferential direction. In FIG. 2, for the purpose of facilitating understanding of the structure of the stent 11, the stent 11 is illustrated in a state expanded in a plane. Furthermore, in FIG. 2, in order to show the cyclic nature of the mesh pattern, the mesh pattern is shown in such a manner that it is virtually repeated more than an actual developed state thereof. In the present specification, the peripheral wall of the stent 11 refers to a part that separates the inside from the outside of a cylinder with a substantially cylindrical shape of the stent 11. Furthermore, the term "cell" also refers to an opening or a compartment that is a part enclosed by the wire-shaped material forming the mesh pattern of the stent 11.

The stent 11 is formed of material having biocompatibility such as stainless steel, tantalum, platinum, gold, cobalt, titanium, or alloys of these. It is particularly preferable for the stent 11 to be formed of materials having a super elastic property such as a nickel titanium alloy.

The stent 11 includes a plurality of circular bodies 13, as a wavy-line pattern body, that is arranged in a longitudinal axis direction LD (i.e. a center axis direction) and a plurality of coiled elements 15 that is arranged between the adjacent circular bodies 13 in the longitudinal axis direction LD. As shown in FIG. 3, the circular bodies 13 include a wavy-line pattern that is formed by connecting, in a circumferential direction, a plurality of waveform elements 17 of substantially V-shape made by coupling two leg portions 17a at an apex 17b. More specifically, the waveform elements 17 of substantially V-shape are connected in a state in which the apices 17b are arranged alternately at the opposite sides.

When viewing in a radial direction RD perpendicular to the axial direction LD, a circular direction CD of the circular bodies 13 is inclined with respect to the radial direction RD. The angle θ at which the circular direction CD of the circular bodies 13 is inclined with respect to the radial direction RD is 30° to 60°, for example.

Both ends of each of the coiled elements 15 are connected with the apices 17b, respectively, at opposite sides of two adjacent circular bodies 13. It should be noted that all of the apices 17b at the opposite sides of the adjacent circular bodies 13 are connected to each other by the coiled element 15. The stent 11 has a so-called closed cell structure. In other words, the two apices 17b that are arranged to be adjacent to each other along the wavy-line pattern among the three apices 17b connected to each other via the leg portions 17a along the wavy-line pattern at one of the circular bodies 13 that are adjacent thereto are respectively connected with the two apices that are arranged to be adjacent to each other along the wavy-line pattern among the three apices connected to each other via the leg portions 17a along the wavy-line pattern at the other one of the circular bodies 13 that are adjacent thereto by way of the coiled elements 15, to form cells. Then, all of the apices 17b of the wavy-line pattern of each of the coiled bodies 13 are shared with three cells.

The plurality of coiled elements 15 is arranged at regular intervals along the circular direction CD of the circular bodies 13. Each of the plurality of coiled elements 15 extends in a spiral manner around the center axis. As shown in FIG. 3, the winding direction (right-handed) of one coiled element 15 (15R) located at one side in the axial direction LD with respect to the circular body 13 and the winding direction (left-handed) of the other coiled element 15 (15L) located at the other side in the axial direction LD are opposite. The length of the one coiled element 15R is longer than the length of the leg portion 17a, but no more than 1.5 times the length of the leg portion 17a. The length of the other coiled element 15L is shorter than the length of the leg portion 17a.

Figure 4:
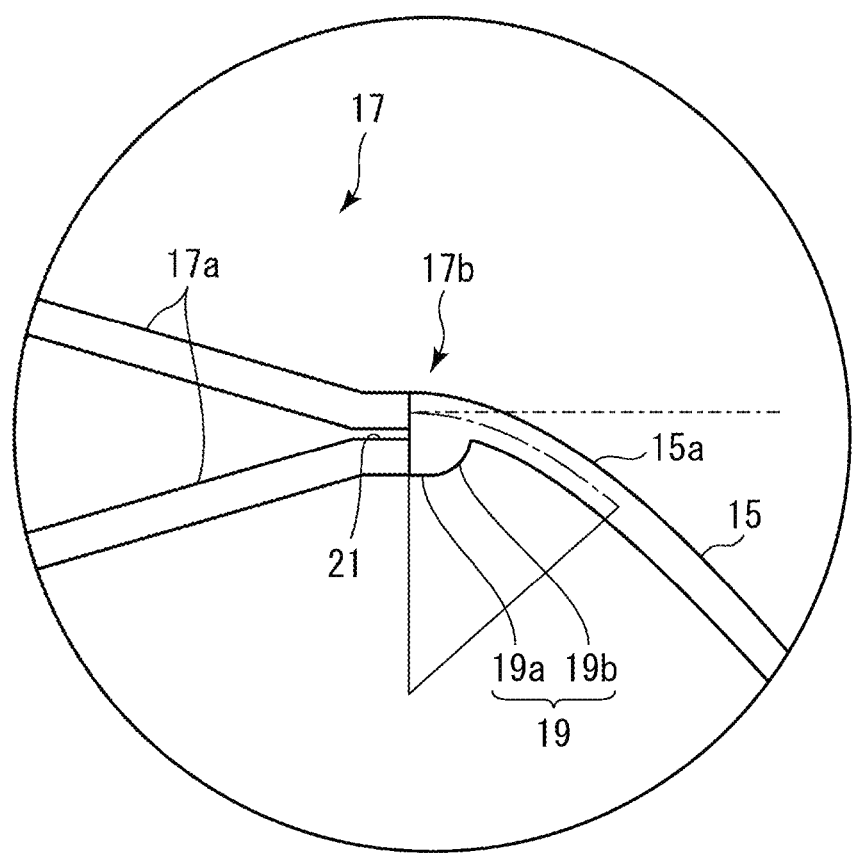
FIG. 4 is a partially enlarged view of the stent shown in FIG. 3.
Figure 5:
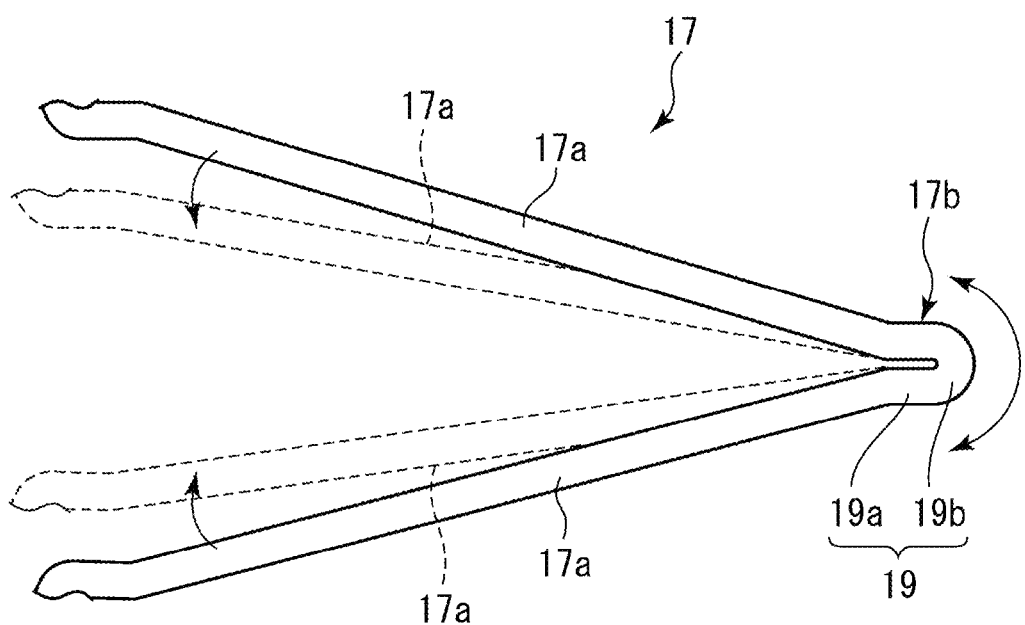
FIG. 5 provides illustrative views showing the matter of deformation occurring at an apex of a waveform element of the circular body of a stent when the stent is radially reduced.
Figure 6A:
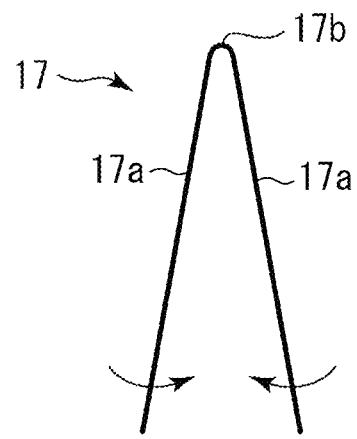
FIG. 6A is a schematic view showing a deformation state of a waveform element during diameter reduction in a case in which a slit is not provided at an apex of a waveform element of the circular body of a stent.
Figure 6B:
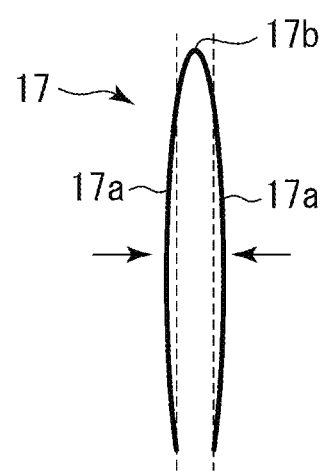
FIG. 6B is a schematic view showing a deformation state of a waveform element during diameter reduction in a case in which a slit is not provided at an apex of a waveform element of the circular body of a stent.
Figure 7A:
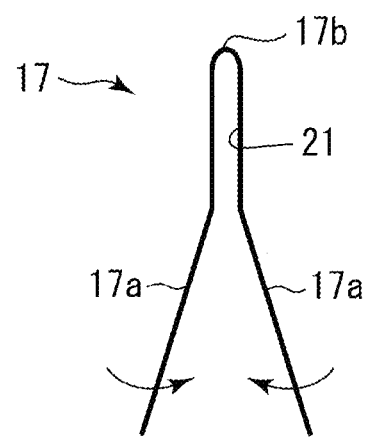
FIG. 7A is a schematic view showing a deformation state of a waveform element during diameter reduction in a case in which a slit is provided at an apex of a waveform element of the circular body of a stent.
Figure 7B:
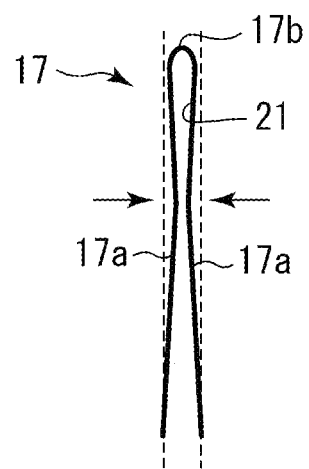
FIG. 7B is a schematic view showing a deformation state of a waveform element during diameter reduction in a case in which a slit is provided at an apex of a waveform element of the circular body of a stent.

FIG. 4 is a partially enlarged view of the stent shown in FIG. 3. FIG. 5 is an illustrative view showing a matter of deformation occurring at an apex of a waveform element of a circular body of a stent when the stent is radially reduced. FIG. 6A is a schematic view showing a deformation state of a waveform element during diameter reduction in a case in which a slit is not provided at an apex of a waveform element of a circular body of a stent. FIG. 6B is a schematic view showing a deformation state of a waveform element during diameter reduction in a case in which a slit is not provided at an apex of a waveform element of a circular body of a stent. FIG. 7A is a schematic view showing a deformation state of a waveform element during diameter reduction in a case in which a slit is provided at an apex of a waveform element of a circular body of a stent. FIG. 7B is a schematic view showing a deformation state of a waveform element during diameter reduction in a case in which a slit is provided at an apex of a waveform element of the circular body of a stent.

As illustrated in FIGS. 4 and 5, a knob portion 19 is formed at the apex 17b of the waveform element 17. The knob portion 19 includes an extension portion 19a extending linearly in the longitudinal axis direction LD and a substantially semicircle portion (tip portion) 19b formed at a tip thereof. The extension portion 19a has a width broader than the width of the coiled elements 15. Furthermore, at the apex 17b of the waveform element 17, a slit 21 is formed that extends in the longitudinal axis direction LD from an inner peripheral portion (a valley portion side of the left side of the waveform element 17 of substantially V-shape in FIG. 4). Therefore, two leg portions 17a are connected to the substantially semicircle portion 19b of the knob portion 19 and a region of the extension portion 19a in which a slit 21 is not provided, via linear portions extending substantially in parallel in the longitudinal axis direction LD. It should be noted that, although it is preferable for the tip portion 19b to be substantially a semicircle portion, it may not be a substantially semicircle portion (not illustrated).

A curve portion 15a is formed at both ends of each of the coiled elements 15. Both ends of each of the coiled elements 15 are respectively connected to the apices 17b (more specifically, the knob portion 19) at the opposite sides of two adjacent circular bodies 13 via the curve portion 15a. As shown in FIG. 4, the curve portions 15a of both ends of the coiled elements 15 have an arc-like shape. The tangential direction of the coiled elements 15 at a connecting end of the coiled element 15 and the apex 17b of the wavy-line pattern of the circular body 13 coincides with the longitudinal axis direction LD.

The center in the width direction of an end of the coiled element 15 and an apex (the center in the width direction) of the apex 17b of the circular body 13 are displaced from each other (do not match). An end edge in the width direction of the end of the coiled element 15 and an end edge in the width direction of the apex 17b of the circular body 13 match.

With the stent 11 having such a structure, superior conformability and diameter reduction are realized, and thus damage to the stent due to the metallic fatigue hardly occurs. The knob portion 19 provided at the apex 17b of the waveform element 17 of the circular body 13 of the stent 11 exerts an effect of reducing metallic fatigue. The slit 21 extending from an inner peripheral portion of the apex 17b of the waveform element 17 of the circular body 13 of the stent 11 exerts an effect of improving diameter reduction of the stent 11.

Structurally speaking, stents of the conventional closed cell structures lack flexibility, and thus there has been a risk of inhibiting blood flow due to a stent buckling in a tortuous blood vessel. Furthermore, if a stent is deformed locally, the deformation propagates not only in a radial direction RD of the stent, but also in the longitudinal axis direction LD, a result of which the stent cannot be deformed independently and locally. For this reason, the stent cannot be adapted to a complicated blood vessel structure such as an aneurysm and causes a space between a peripheral wall of the stent and a blood vessel wall, a result of which the stent easily slides in an intravascular lumen due to the deformation accompanied with the pulsation of a blood vessel, and may also cause movement (migration) of the stent after the placement therein.

On the other hand, when the stent 11 according to the embodiment is deformed from an expanded state to a radially reduced state (a crimped state), the wavy-line pattern of the circular body 13 is folded so as to enter a compressed state, and the coiled element 15 is made to be laid in the longitudinal axis direction LD as a coiled spring and enters a state being pulled in the longitudinal axis direction LD. When viewing a single piece of the waveform element 17 of the wavy-line pattern of the circular body 13 of the stent 11, as illustrated in FIG. 5, the waveform element 17 deforms to be open and closed such as a tweezer upon the diameter reduction and expansion of the stent 11.

In a case in which the slit 21 is not provided at a valley side portion of a base of the waveform element 17 (an inner peripheral portion of the apex 17b) as shown in FIG. 6A, when deforming the stent 11 so as to close the waveform element 17 to radially reduce the stent 11, center portions of the leg portions 17a swell outward in a barrel-like shape and thus easily deform, as illustrated in FIG. 6B. If the waveform element 17 is swollen in a barrel-like shape in this way, the swollen portions in a barrel-like shape of the leg portions 17a of the adjacent waveform elements 17 in a circumferential direction in the circular body 13 come into contact with each other when radially reducing the stent 11.

This contact prevents the stent 11 (more specifically, the circular body 13) from radially reducing, which leads to the degradation of the ratio of diameter reduction. On the other hand, the slit 21 is provided at a base portion of the waveform element 17 of the circular body 13 as illustrated in FIG. 7A in the stent 11 according to the embodiment. Therefore, when radially reducing the stent 11, as illustrated in FIG. 7B, the stent 11 is deformed so that the leg portions 17a of the waveform element 17 adjacent in a circumferential direction in the circular body 13 bring less contact with each other, a result of which the ratio of diameter reduction can be improved.

As described above, the waveform element 17 deforms to be open and closed such as a tweezer upon the diameter reduction and expansion of the stent 11 as shown in FIG. 5. Therefore, upon crimping and expansion of the stent 11, the deformation concentrates on the apex so that the strain due to material deformation occurs intensively at this part. Therefore, in a case of repeating diameter reduction and expansion of the stent 11 or in a case in which the stent 11 repeatedly receives load accompanied with deformation due to blood flow in a blood vessel or pulsation of a wall of a blood vessel, excessive metallic fatigue tends to occur at the apex 17b of the waveform element 17. Therefore, in order to reduce the risk of metallic fatigue occurring, the shape of the apex 17b is modified for an improvement in the stent 11 so as to reduce the strain occurring at the apex 17b.

Upon diameter reduction and expansion of the stent 11, since the waveform element 17 becomes opened and closed around a valley side portion of the base portion (inner peripheral portion), the strain of the apex 17b of the waveform element 17 occurs greatly particularly at an outer peripheral portion in the region of the apex 17b (an outside of the apex 17b shown by a curve with arrows at the both ends of the curve in FIG. 5). Here, the strain e is represented by the following equation with the length before deformation being $l_0$ and the deformation amount being u.

$$e = u/l_0$$

Therefore, in order to reduce the risk of metallic fatigue occurring at the apex 17b of the stent 11, it is only necessary to reduce the strain occurring at the apex 17b upon diameter reduction and expansion of the stent 11.

Figure 8:
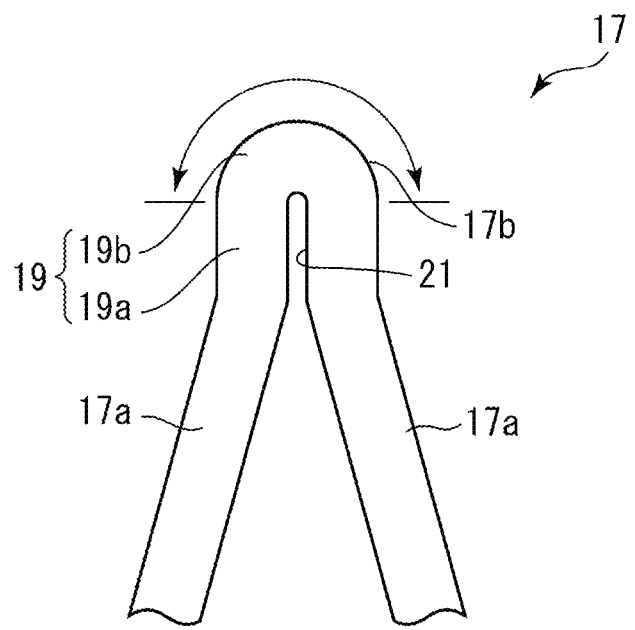
FIG. 8 is a partially enlarged view showing a first embodiment of an apex of a waveform element of the circular body of the stent.
Figure 9:
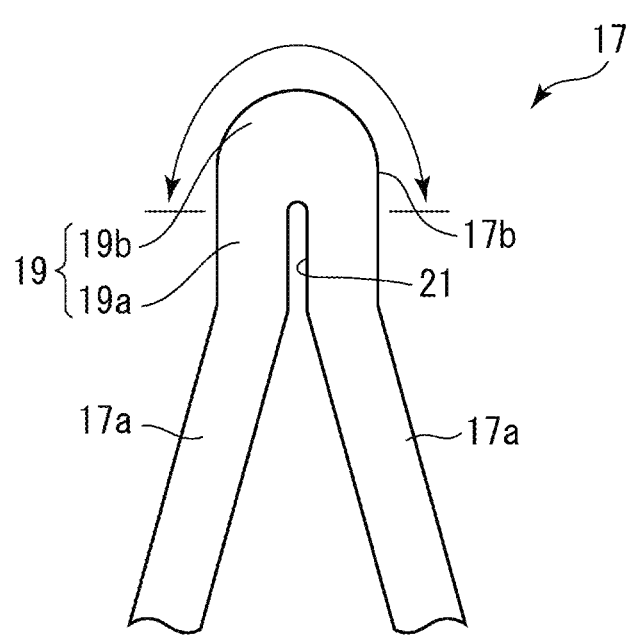
FIG. 9 is a partially enlarged view showing a second embodiment of an apex of a waveform element of the circular body of the stent.
Figure 10:
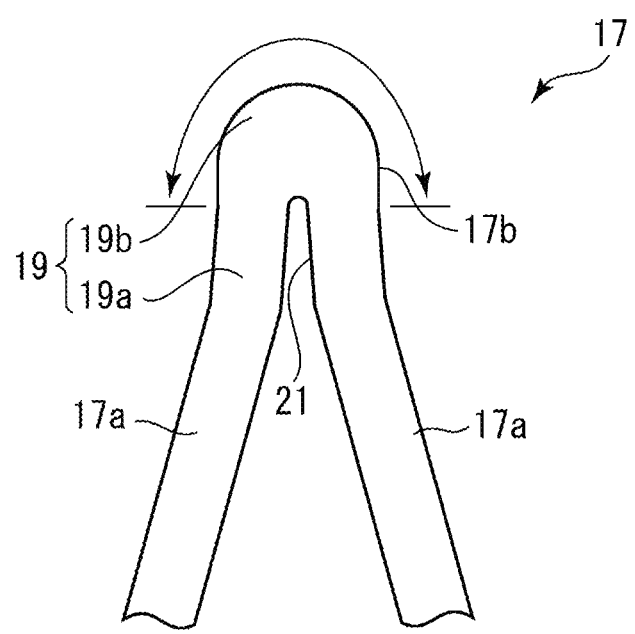
FIG. 10 is a partially enlarged view showing a third embodiment of an apex of a waveform element of the circular body of the stent.

FIG. 8 is a partially enlarged view showing a first embodiment of an apex of a waveform element of the circular body of the stent. FIG. 9 is a partially enlarged view showing a second embodiment of an apex of a waveform element of the circular body of the stent. FIG. 10 is a partially enlarged view showing a third embodiment of an apex of a waveform element of the circular body of the stent.

When assuming that the same deformation amount u is imparted upon diameter reduction, it is possible to reduce the strain occurring at the apex 17b by increasing the length corresponding to $l_0$. Furthermore, the deformation of the waveform element 17 is made at a valley side portion of the base portion of the waveform element 17 (inner peripheral portion), and a portion that substantially contributes to the deformation is a peak side portion of the apex 17b of the waveform element 17 (the range shown by a curve with arrows at both ends of the curve on the upper side in FIGS. 8 to 10), specifically an outer peripheral portion. Therefore, as shown in FIGS. 8 to 10, it is configured in the stent 11 such that the knob portion 19 including the extension portion 19a and the substantially semicircle portion 19b and having a width greater than the width of the coiled element 15 is formed at the apex 17b to allow the apex portion 17b to extend in the longitudinal axis direction LD.

More specifically, the extension portion 19a extending in the longitudinal axis direction LD is provided between the leg portions 17a of the waveform element 17 and the substantially semicircle portion 19b forming the apex 17b so as to offset the apex 17b outward from the valley side portion of the base portion of the waveform element 17 (inner peripheral portion) as a deformation base point. The outer peripheral portion of the apex 17b is made to extend with such a configuration. In order to prevent adjacent knob portions 19 in a circumferential direction from blocking diameter reduction due to coming into contact with each other upon diameter reduction, as shown in FIGS. 8 to 10, it is desirable for the extension portion 19a to be formed by way of a linear portion extending in the longitudinal axis direction LD.

It should be noted that, in a case in which the slit 21 extending from the inner peripheral portion of the apex 17b is formed at the apex 17b of the waveform element 17, as shown in FIGS. 7A and 7B, the deformation of the waveform element 17 takes place around a tip of the slit 21 (an upper end of the slit 21 in FIGS. 8 to 10). A main portion involved in the deformation accompanied with crimping and expansion corresponds to a portion that is located more outside than the tip of the slit 21 of the waveform element 17. Therefore, it is more preferable to configure such that the length of the extension portion 19a is longer than the length of the slit 21 and the extension portion 19a extends beyond the tip of the slit 21, as shown in FIG. 9, than to configure such that the length of the extension portion 19a is the same as the length of the slit 21 or shorter than the length of the slit 21, as shown in FIG. 8.

As shown in FIGS. 8 and 9, opposite side edges of the slit 21 are linear extending substantially in parallel. It should be noted that, as shown in FIG. 10, the opposite side edges of the slit 21 may not extend substantially in parallel (for example, the opposite side edges may become slightly wider toward the leg portions 17a). In addition, the opposite side edges of the slit 21 may not be linear (not illustrated).

Furthermore, in a case of the stent 11 being formed of a super elastic alloy such as a nickel titanium alloy, as shown in FIG. 9, it can be configured so as to provide the knob portion 19 at the apex 17b of the waveform element 17 of the circular body 13 of the stent 11 and have the length of the extension portion 19a of the knob portion 19 longer than the length of the slit 21. With such a configuration, it is possible to extract the super elastic property of the super elastic alloy to a maximum extent and suppress a change in expansive force with respect to a change in the outer diameter of the stent 11.

In a case in which the slit 21 is provided at the apex 17b of the waveform element 17 of the circular body 13 of the stent 11, it is configured such that the length of the extension portion 19a of the knob portion 19 provided at the apex 17b is longer than the length of the slit 21 so that the volume ratio of the phase transformation to martensite phase at a neighboring portion of the slit 21 upon loading increases. Therefore, it is configured for the stent 11 to include the waveform element 17 having the apex 17b as shown in FIG. 9, so that it is possible to realize the stent 11 for which a change in expansive force with respect to a change in a diameter of the stent 11 is gentle and with less change in expansive force with different diameters of blood vessels.

The curve portion 15a provided at both ends of the coiled element 15 of the stent 11 makes the deformation of the coiled element 15 at the connected portion with the circular body 13 further smoother, a result of which it exerts an effect of further improving the diameter reduction of the stent 11.

When radially reducing the stent 11, the coiled element 15 is deformed so as to elongate in the longitudinal axis direction LD. Therefore, in order to improve the flexibility of the stent 11, it is necessary to design the stent 11 so that the connecting portion of the apex 17b of the circular body 13 and the coiled element 15 becomes flexible. In stent 11, the curve portion 15a having a circular shape at both ends of the coiled element 15 is provided and the apex 17b of the circular body 13 is connected with the coiled element 15 via the curve portion 15a. Upon the diameter reduction of the stent 11, the curve portion 15a is bent and deformed, a result of which the flexible deformation of the coiled element 15 becomes possible, which leads to an improvement in diameter reduction.

Furthermore, the configuration in which the tangential direction of the curve portion 15a at the connecting end at which the coiled element 15 connects with the apex 17b of the circular body 13 coincides with the longitudinal axis direction LD exerts an effect of making a change in expansive force with respect to a change in the diameter of the stent 11 gentle.

The coiled element 15 is deformed like a coiled spring to elongate in the longitudinal axis direction LD, which allows for the deformation in a radial direction RD accompanied with the diameter reduction of the stent 11. Therefore, by matching the tangential direction of the curve portion 15a at the connecting end at which the circular body 13 connects with the coiled element 15 with the longitudinal axis direction LD, it becomes possible to effectively exhibit deformation properties of the coiled element 15 in the longitudinal axis direction LD. Since it is configured such that the coiled element 15 can be deformed smoothly in the longitudinal axis direction LD, the diameter reduction and expansion of the stent 11 is facilitated. Furthermore, since natural deformation in the longitudinal axis direction LD of the coiled element 15 is facilitated, it is possible to prevent unpredictable deformation resistance from occurring, which exerts an effect of making the response of expansive force with respect to a change in the diameter of the stent 11 gentle.

The stent 11 is inserted into a catheter in a state of being radially reduced, extruded by an extruder such as a pusher and moved in the catheter, and expanded at a site of pathology. At this moment, the force in the longitudinal axis direction LD applied by the extruder interacts between the circular body 13 and the coiled element 15 of the stent 11 to propagate over the entire stent 11.

The stent 11 having the abovementioned structure is produced by laser-machining a material having biocompatibility, and more preferably, a tube made of a super elastic alloy. When producing a stent made of a super elastic alloy tube, in order to reduce production cost, it is preferable to produce the stent 11 by expanding an approximately 2 to 3 mm tube to a desirable diameter and performing shape-memory treatment after laser-machining. However, the method of producing the stent 11 is not limited to laser-machining and includes other methods such as cutting processing.

Next, an operational effect according to the configuration of "when viewing in the radial direction RD perpendicular to the axial direction LD, the circular direction CD of the circular bodies 13 is inclined with respect to the radial direction RD." is explained. First, the configuration of the stent 11 is described in which, when viewing in the radial direction RD, the circular direction CD of the circular body 13 follows the radial direction RD (not inclined with respect to the radial direction RD).

Figure 11A:
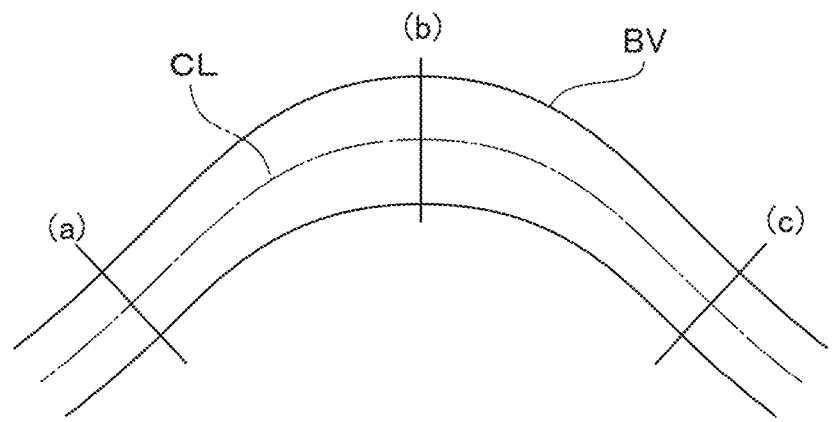
FIG. 11A shows a central axis of a cross section of a stent and a side view of a blood vessel.
Figure 11B:
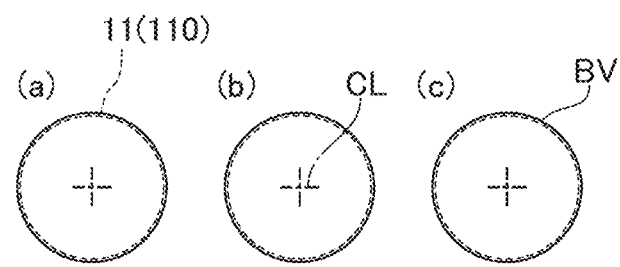
FIG. 11B is a schematic view of a cross section of a stent where a central axis is not displaced.
Figure 11C:
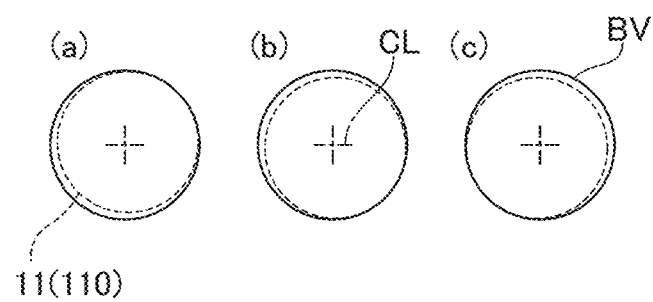
FIG. 11C is a schematic view of a cross section of a stent where a central axis is displaced.
Figure 12:
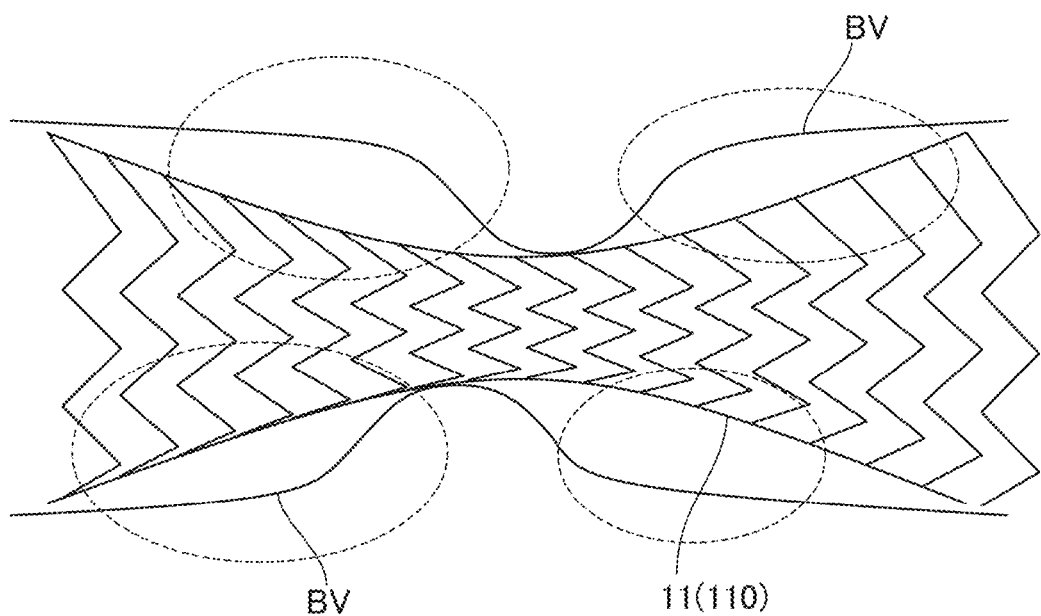
FIG. 12 is a schematic view showing a malapposition.
Figure 13:
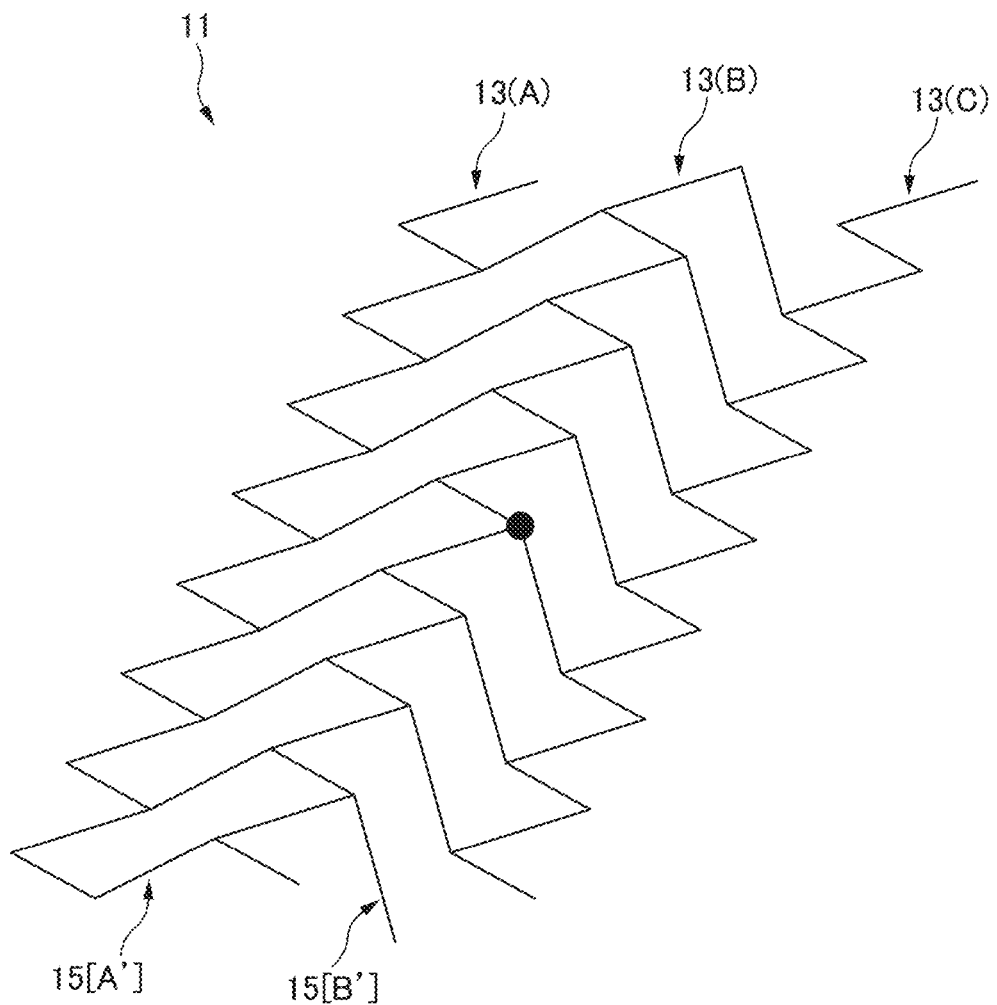
FIG. 13 is a schematic view of a developed view of a highly flexible stent in an unloaded state according to a first embodiment of the present invention.
Figure 15:
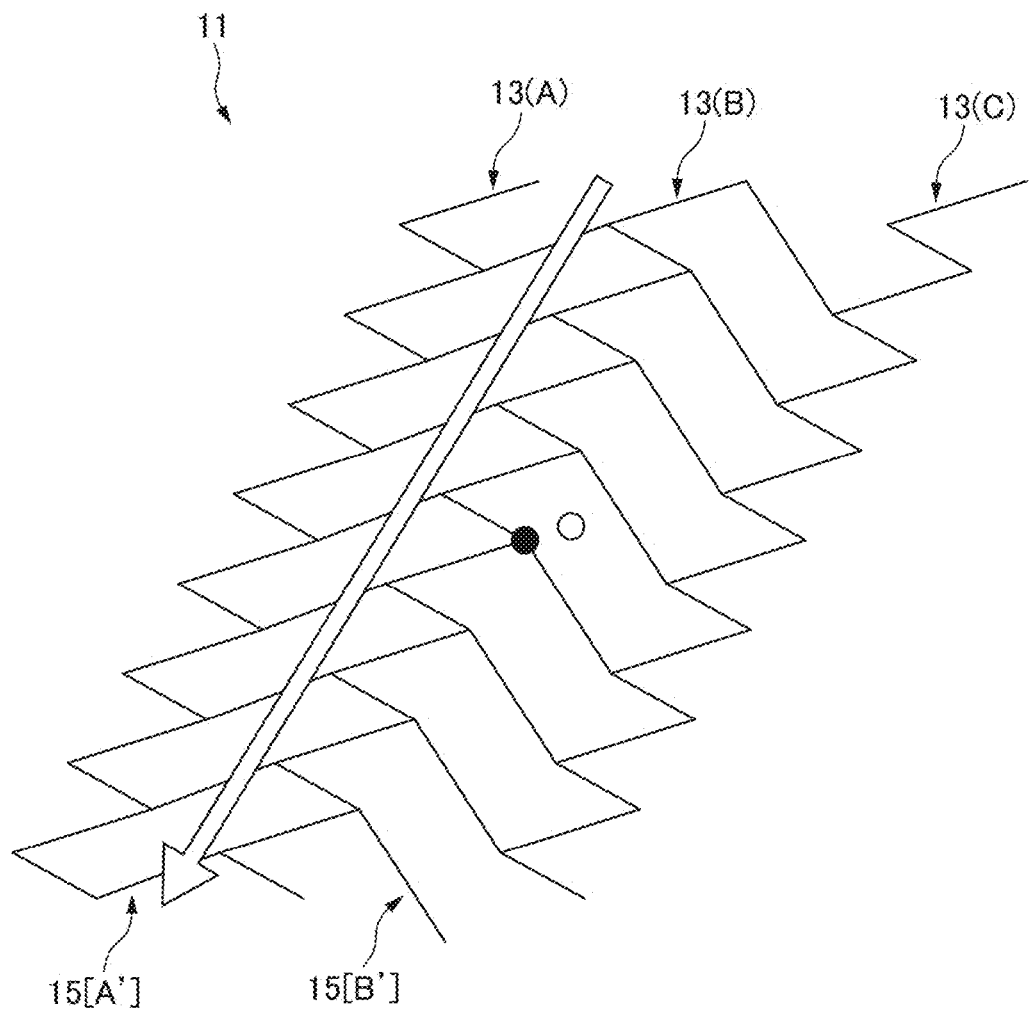
FIG. 15 is a schematic view showing the behavior of the center in the figure of a cross section of the bent stent.
Figure 18:
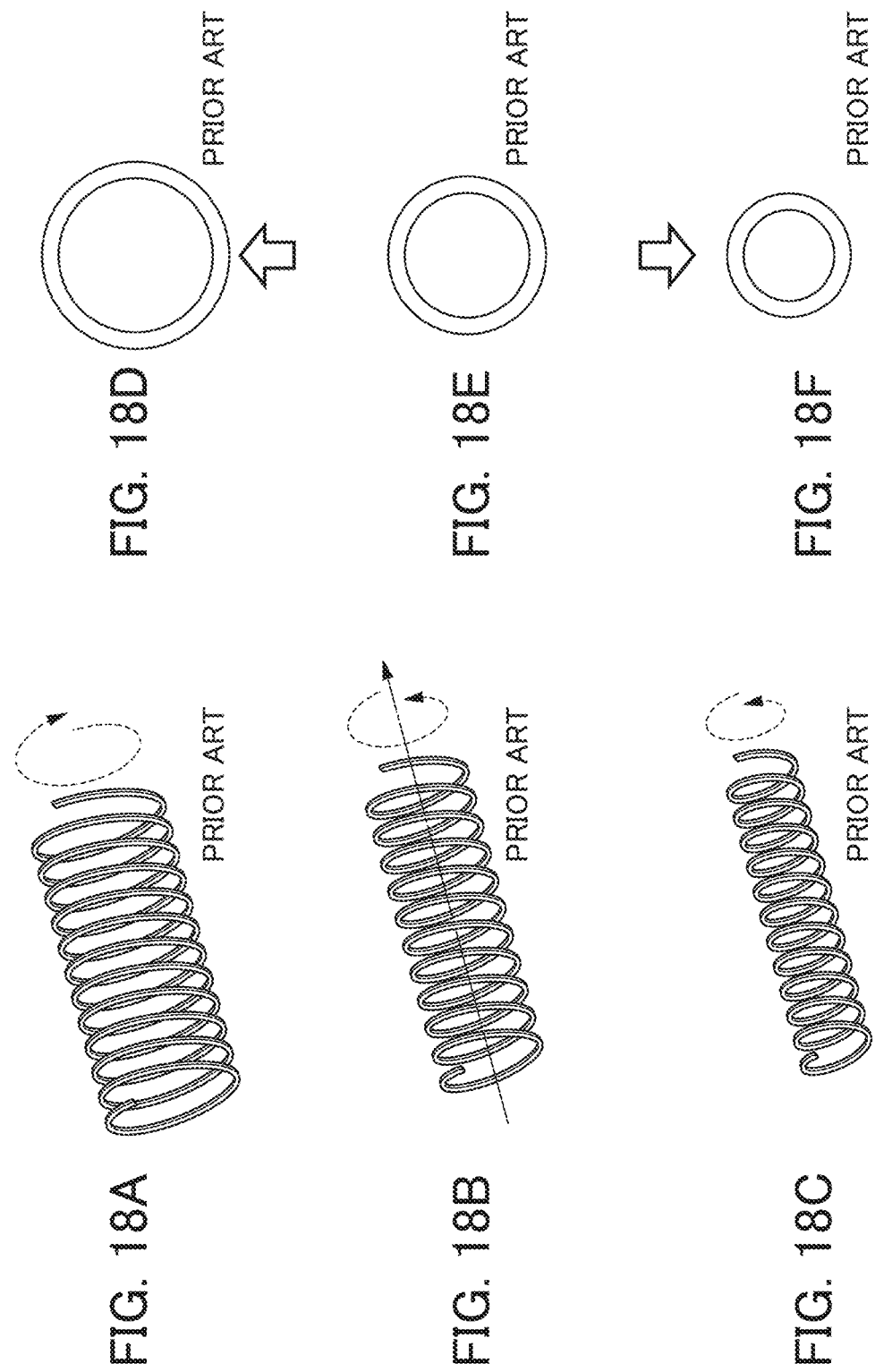
FIGS. 18A, 18B, 18C, 18D, 18E, and 18F is a schematic view showing the behavior of a distorted deformation in a case of assuming a deformation with a coiled element of a stent as a part of a left-hand spring structure.
Figure 19:
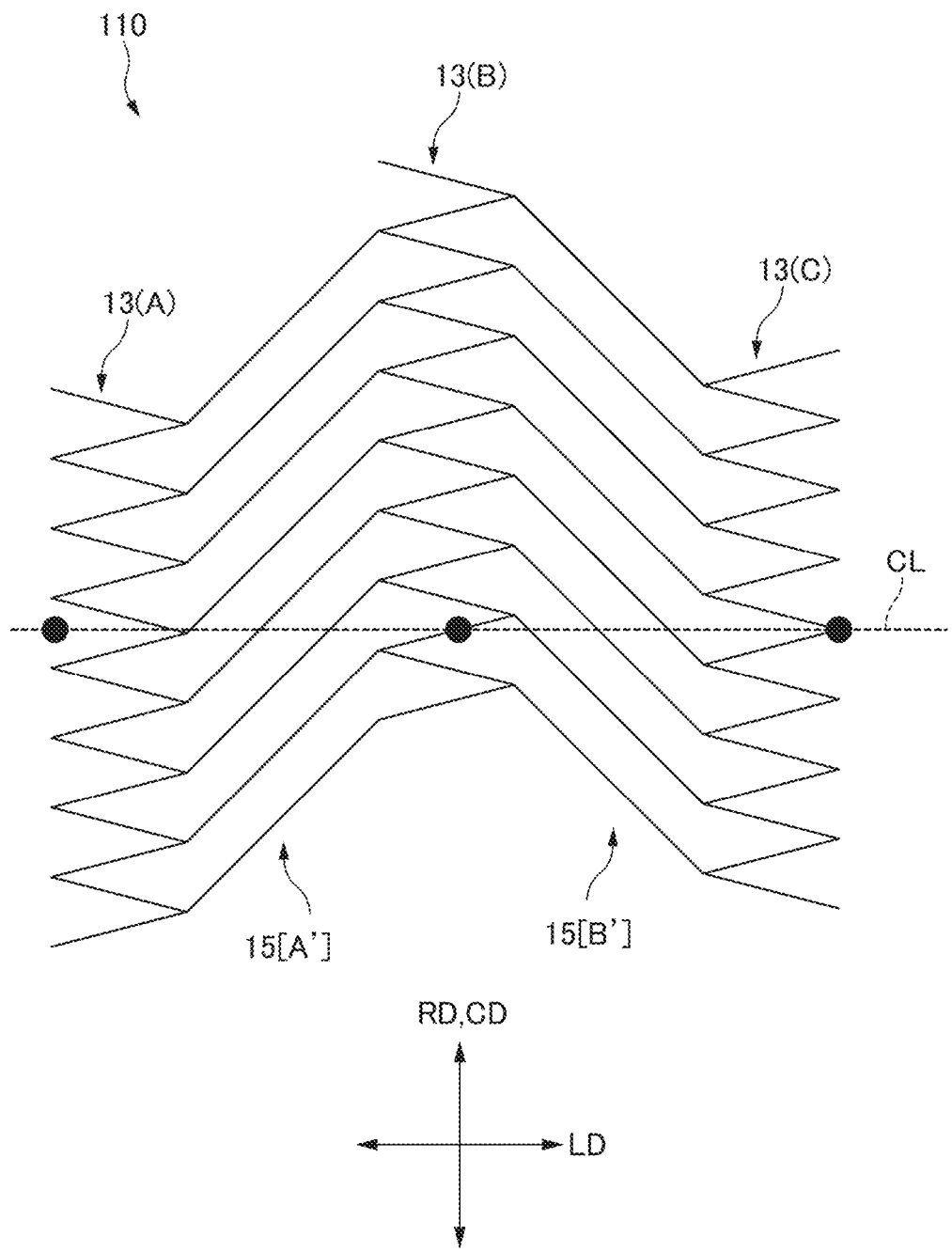
FIG. 19 is a developed view of a conventional stent in which a circular direction of a circular body is not inclined with respect to a radial direction.
Figure 20:
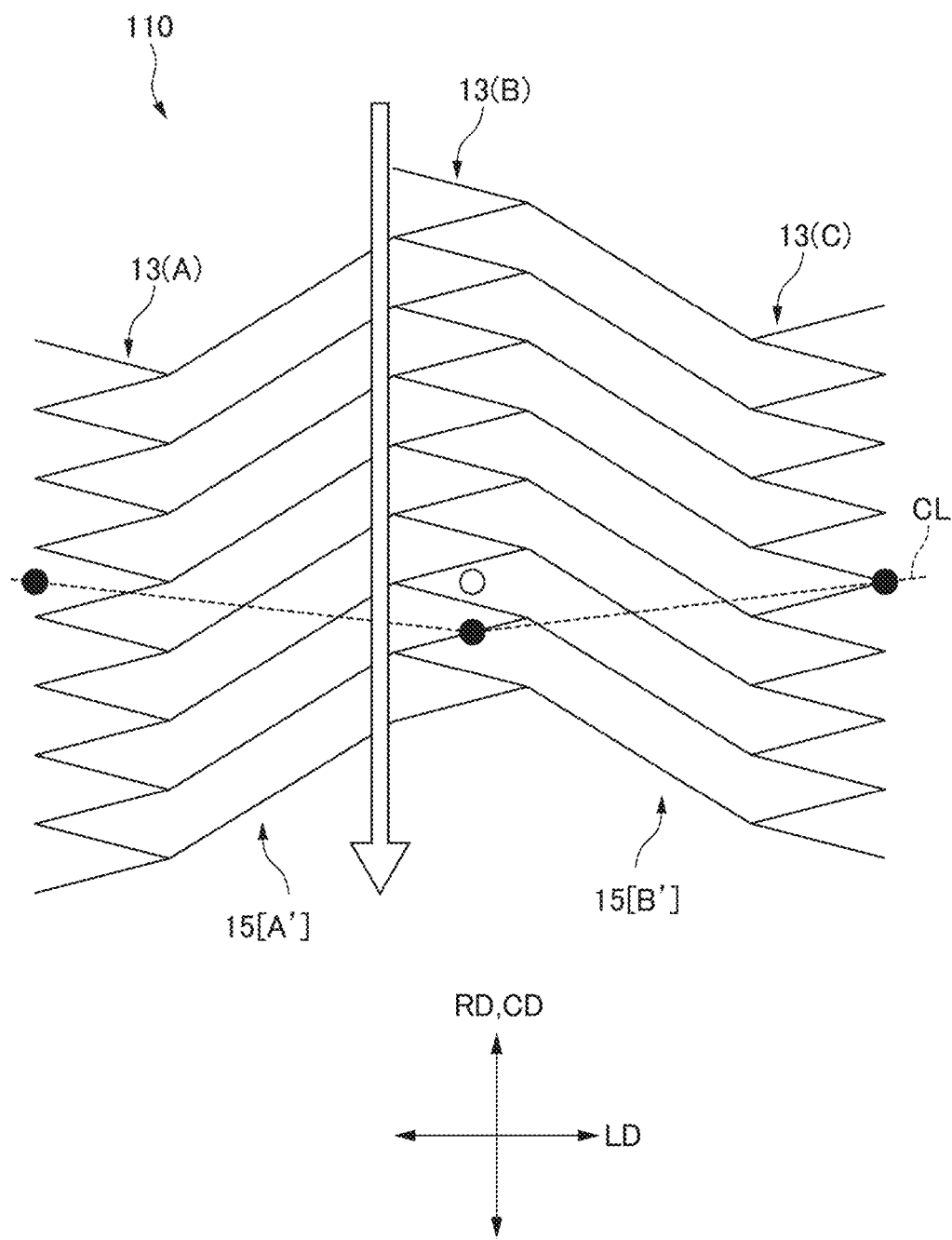
FIG. 20 is a developed view showing a state after bending deformation being applied to the stent shown in FIG. 19.

FIG. 11A shows a central axis of a cross section of the stent and a side view of a blood vessel. FIG. 11B is a schematic view of a cross section of the stent where the central axis is not displaced. FIG. 11C is a schematic view of a cross section of the stent where the central axis is displaced. FIG. 12 is a schematic view showing a malapposition. FIG. 13 is a schematic view of a developed view of a highly flexible stent in an unloaded state according to a first embodiment of the present invention. FIG. 14 is a schematic view showing the behavior of a coiled element and the center of the figure when the stent shown in FIG. 13 is bent. FIG. 15 is a schematic view showing a behavior of the center of the figure of a cross section of the stent bent. FIG. 16 is a schematic view showing a behavior in a case in which a distortion in a right-hand direction is applied to the stent shown in FIG. 13. FIG. 17 is a schematic view showing a behavior in a case in which a distortion in a left-hand direction is applied to the stent shown in FIG. 13. FIGS. 18A to 18F is a schematic view showing a behavior of a distorted deformation in a case of assuming a deformation with a coiled element of a stent as a part of a left-hand spring structure. FIG. 19 is a developed view of a conventional stent in which a circular direction of a circular body is not inclined with respect to a radial direction. FIG. 20 is a developed view showing a state after bending deformation being applied to the stent shown in FIG. 19.

Regarding a stent 110 (refer to FIG. 19) with a structure in which the circular direction CD of the circular body 13 is not inclined with respect to the radial direction RD, in an intracranial blood vessel, which is strongly curved, the center axis CL of a cross section of the stent 11 (110) is easily displaced, as shown in FIG. 11A to 11C. It should be noted that, in each drawing, a solid line indicates a blood vessel BV, a dashed-dotted line indicates the center axis CL of the stent 11 (110), and a dashed line indicates a cross section of the stent 11 (110).

In FIG. 19, a position at the center of the figure of the cross section of the circular body 13 is shown by a black circle. A line passing through the centers of the figures (black circles) of the cross sections of each circular body 13 corresponds to the center axis CL of the stent 110. Each of the circular bodies 13 are denoted by (A), (B), and (C) from the left in the figure. The coiled elements 15 connected with the adjacent circular bodies 13, 13 are denoted by (A') and (B') from the left in the figure. When bending load is applied to the abovementioned stent 110, a back side portion of the stent 110 exhibits a deformation behavior as if being pulled in the axial direction LD.

In FIG. 20, when bending is applied to the stent 110, the circular body 13(B) moves in a circumferential direction. This is due to the coiled elements 15 connecting between the circular body 13(A) and the circular body 13(B) or between the circular body 13(B) and the circular body 13(C) being pulled and expanded so as to move the circular body 13(B) in the direction of the white arrow. In this way, the center of the figure before the deformation (white circle) moves to the position of the black circle after the deformation. At this time, as shown in FIG. 20, the center axis CL passing through the centers of figures shown by the black circles in each of the circular bodies 13(A), 13(B), and 13(C) after deformation becomes zigzagged. This causes the center of the figure to move to a displaced position from the center of the cross section of a blood vessel when the stent 110 is bent. At this time, if the center of the figure of the cross section of the stent becomes displaced from the center of the cross section of the blood vessel, a strut of the stent floats from a blood vessel wall BV (generation of malapposition).

If the center of the figure of the cross section of the stent 11 is displaced when the stent 11 is bent, the adhesion of the stent 11 to the blood vessel wall BV decreases, which causes malapposition (refer to FIG. 12). The displacement of the center of the figure of the cross section of the stent 11 is caused by transmission of a force working towards the circumferential direction. Malapposition refers to a strut of the stent 11 floating (moving away) from the blood vessel wall BV as shown in FIG. 12.

Stagnation of blood flow occurs between the stent 11 and the blood vessel wall BV, which leads to the generation of a blood clot. Due to this, blood clots are generated excessively at an intravascular lumen of the stent 11 (in-stent restenosis) or the blood clots flow to a terminus thereof, a result of which it is likely that problems such as blockage in a blood vessel will occur. (Background Incidence of Late Malapposition After Bare-Metal Stent Implantation, etc.) Furthermore, since the stress distribution of the stent 11 differs locally, the risk of damaging a blood vessel wall, etc., increases.

As shown in FIGS. 13 and 14, when the coiled element 15 (B') is pulled in a circumferential direction of (a), in order to correct for the matter of being pulled in the circumferential direction of (a), the circular body 13 (A) tries to deform the circular body 13 (B) in a direction of (b). For this reason, as a result, since the center of the figure also moves in the axial direction LD (moving from the black circle to a white circle), as shown in FIG. 15, it is possible to reduce malapposition due to the displacement of the center of the figure.

On the other hand, in regard to the stent 11 of the present embodiment, since the circular body 13 having the wavy-line pattern can be easily deformed in a circumferential direction, the stent 11 can be flexibly adapted to contraction and expansion in a radial direction. Furthermore, the coiled element 15 connecting between the adjacent circular bodies 13, 13 extends in a spiral manner around the central axis and is deformed like a coiled spring. For this reason, when the stent 11 is bent, the coiled element 15 elongates at the outside of a bent portion and contracts at the inside of the bent portion. With such a configuration, flexible bending deformation of the overall stent 11 in the longitudinal axis direction LD is made possible.

Furthermore, an external force given to the stent 11 locally and a resulting deformation propagate in a radial direction RD by way of the circular body 13 of the wavy-line pattern and propagate in a circumferential direction by way of the coiled element 15. Therefore, the circular body 13 and the coiled element 15 can be deformed almost independently at each site. With such a configuration, the stent 11 can be placed so as to be adapted to a site of pathology in a blood vessel structure even in a case in which the stent 11 is adapted to a site of pathology in a particular blood vessel such as a brain aneurysm. For example, in a case in which the stent 11 is placed at the site of a brain aneurysm, the circular body 13 of the wavy-line pattern is placed at a neck portion of a knob. In this way, the circular body 13 expands in a radial direction RD and develops in a space of the knob, so that the stent 11 can be fastened securely at this site.

Furthermore, the coiled element 15 is in contact with a peripheral wall of a blood vessel along a shape of the blood vessel wall so as to serve as an anchor. Therefore, the risk of the stent 11 migrating is reduced. Furthermore, since the stent 11 has a closed cell structure, even when it is adapted to a bent site, it is possible to reduce the risk of the strut of the stent 11 protruding outward in a flared shape to damage a blood vessel wall and the strut of the stent 11 causing inhibition of blood flow.

Furthermore, as shown in FIG. 16, when a left-handed distortion is applied to the stent 11, a force acts in such a manner that the one coiled element 15 (A') is pulled in a perpendicular direction with respect to the cross section of an element wire of a spring. For this reason, the element wire is deformed so as to be wound in a direction of (d) in FIG. 16 (i.e. in the circumferential direction) and exhibits the behavior of being radially reduced in the radial direction RD. On the other hand, a force acts in such a manner that the other coiled element 15 (B') is compressed in a perpendicular direction with respect to the cross section of the element wire of a spring. For this reason, the element wire is deformed so as to be pulled away in a direction of (e) in FIG. 16 (i.e. in the circumferential direction) and, as a result, exhibits the behavior of a diameter being expanded in a radial direction RD. As a result, since the deformations of the one coiled element 15 (A') and the other coiled element 15 (B') at each unit are compensated by each other, the deformation amount in the radial direction RD of the coiled element 15 in the stent 11 as a whole is suppressed.

On the other hand, as shown in FIG. 17, when a right-handed distortion is applied to the stent 11, a force acts in such a manner that the other coiled element 15 (B') is pulled in a perpendicular direction with respect to the cross section of the element wire of a spring. For this reason, the element wire is deformed so as to be wound in the direction of (f) of FIG. 17 (i.e. in the circumferential direction) and exhibits the behavior of being radially reduced in the radial direction RD. On the other hand, a force acts in such a manner that the other coiled element 15 (A') is compressed in a perpendicular direction with respect to the cross section of the element wire of a spring. For this reason, the element wire is deformed so as to be pulled away in the direction of (g) in FIG. 17 (i.e. in the circumferential direction) and, as a result, exhibits the behavior of a diameter being expanded in a radial direction RD. As a result, since the deformations of the one coiled element 15 (A') and the other coiled element 15 (B') are compensated by each other, the deformation amount in the radial direction RD of the coiled element 15 in the stent 11 as a whole is suppressed.

In this way, by introducing the coiled element 15R and 15L (15 (A'), 15 (B')) of which the winding directions are opposite to each other, it is possible to reduce the difference in the deformation amounts in the radial direction RD between the left and right distorted deformations.

Furthermore, in the present embodiment, the length of the coiled element 15 is shorter than the length of the leg portion 17a or not too long. For this reason, as compared with the case in which the length of the coiled element 15 is considerably longer than the length of the leg portion 17a, when being distorted in a direction opposite to the winding direction of the coiled element 15, it is not likely that the stent 11 swells as a whole, a result of which malapposition is less likely to occur. Furthermore, since there are few portions at which the force in the radial direction RD in the stent 11 does not act, with regards to the distribution of the force in the radial direction RD in the stent 11, cells at which a high force acts locally and portions at which a force substantially becomes 0 (zero) locally are less likely to occur.

Regarding the materials for a stent, a material having high rigidity and high biocompatibility in itself are preferable. Such materials include, for example, titanium, nickel, stainless steel, platinum, gold, silver, copper, iron, chrome, cobalt, aluminum, molybdenum, manganese, tantalum, tungsten, niobium, magnesium, and calcium, or alloys including these. Furthermore, for such materials, synthetic resin materials such as polyolefins such as PE and PP, polyamide, polyvinyl chloride, polyphenylene sulfide, polycarbonate, polyether, and polymethyl methacrylate can be used. Furthermore, for such materials, biodegradable resins such as polylactic acid (PLA), polyhydroxybutyrate (PHB), polyglycolic acid (PGA) and polyε-caprolactone can be used.

Among these, titanium, nickel, stainless steel, platinum, gold, silver, copper and magnesium or alloys including these are preferable. Alloys include, for example, Ni—Ti alloy, Cu—Mn alloy, Cu—Cd alloy, Co—Cr alloy, Cu—Al—Mn alloy, Au—Cd—Ag alloy and Ti—Al—V alloy. Furthermore, alloys include, for example, alloys of magnesium with Zr, Y, Ti, Ta, Nd, Nb, Zn, Ca, Al, Li and Mn. Among these alloys, Ni—Ti alloy is preferable.

A stent may include a medical agent. Here, a stent including a medical agent refers to the matter of the stent releasably supporting a medical agent so that the medical agent can be eluted. Although the medical agent is not limited, a physiologically active substance can be used, for example. Physiologically active substances include, for example, drugs for suppressing intimal hyperplasia, anticancer drugs, an immune-suppressing drugs, antibiotic drugs, antirheumatic drugs, antithrombogenic drugs, HMG-CoA reductase inhibitors, ACE inhibitors, calcium antagonist agents, antilipemic drugs, anti-inflammatory drugs, integrin inhibitors, antiallergic agents, antioxidant agents, GPIIbIIIa antagonist drugs, retinoid, flavonoid, carotenoid, lipid improvers, inhibitors of DNA synthesis, tyrosine kinase inhibitors, antiplatelet drugs, vascular smooth muscle growth inhibitors, anti-inflammatory agents, interferons, etc. It is also possible to use a plurality of these drugs.

"A drug for suppressing intimal hyperplasia" to prevent recurrent stenosis is preferable in particular. A drug for suppressing intimal hyperplasia includes, for example, a drug possessing an effect of suppressing blood vessel intimal hyperplasia that does not inhibit the growth of endothelial cells. Such a drug includes, for example, Argatroban; (2R, 4R)-4-methyl-1-[N2-((RS)-3-methyl-1,2,3,4-tetrahydro-8-quinolinesulfonyl)-L-arginine]-2-piperidinecarboxylic acid (Japanese Unexamined Patent Application, Publication No. 2001-190687; International Publication No. WO2007/058190), Ximelagatran, Melagatoran, Dabigatran, Dabigatran etexilate, rapamycin, everolimus, biolimus A9, zotarolimus, tacrolimus, paclitaxel, statin, etc.

In order for the stent to involve a drug, the surface of the stent may be coated with the drug. In this case, the surface of the stent may be directly coated with a drug, or the stent may be coated with polymer in which a drug is contained. Furthermore, grooves or holes for storing a drug in a stent may be provided as a reservoir, and the drug or a mixture of the drug and polymer may be stored therein. A reservoir for storage has been disclosed in Japanese Unexamined Patent Application (Translation of PCT Publication), Publication No. 2009-524501.

The polymers used in this case include, for example, flexible polymers having a glass transition temperature of −100° C. to 50° C. such as silicone rubber, urethane rubber, fluorine resin, polybutyl acrylate, polybutyl methacrylate, acrylic rubber, natural rubber, ethylene-vinyl acetate copolymer, styrene-butadiene block copolymer, styrene-isoprene block copolymer and styrene-isobutylene block copolymer, and biodegradable polymers such as polylactic acid, poly (lactic acid-glycolic acid), polyglycolic acid, poly(lactic acid-ε-caprolactone), poly(glycolic acid-trimethylene carbonate) and poly-β-hydroxybutyric acid.

The mixture of polymer and a drug can be performed by dispersing the drug in polymer, for example, and can be performed following the disclosure of PCT International Publication No. WO2009/031295. A drug contained in a stent is delivered to an affected area via the stent and released in a controlled manner.

It is possible to coat a diamond like carbon layer (DLC layer) on the surface of a stent. The DLC layer may be a DLC layer including fluorine (F-DLC layer). In this case, it becomes a stent that excels in antithrombogenicity and biocompatibility.

Next, a method of using the stent 11 is described. A catheter is inserted into a blood vessel of a patient and the catheter is delivered to a site of pathology. Then, the stent 11 is radially reduced (crimped) and placed in the catheter. The property of the diameter reduction of the stent 11 is improved by multiple and synergistic effects due to the wavy-line pattern of the circular body 13, the slit 21 formed at the apex 17b of the circular body 13, the curve portion 15a of the coiled element 15, and the configuration in which a tangential direction of the curve portion 15a at a connecting end coincides with the longitudinal axis direction LD. Therefore, it becomes easier to insert the stent 11 into a narrow catheter and also becomes possible to apply the stent 11 to narrower blood vessels, as compared to conventional stents.

Next, the stent in a state of being radially reduced is pushed out along a lumen of the catheter using an extruder such as a pusher and the stent 11 is extruded from a tip of the catheter and expanded at a site of pathology. The flexibility upon delivery of the stent 11 is improved by multiple and synergistic effects due to the configuration in which a plurality of the circular bodies 13 are connected with the coiled elements 15, the curve portion 15a of the coiled element 15, and the configuration in which a tangential direction of the curve portion 15a at a connecting end coincides with the longitudinal axis direction LD. Therefore, even in a case in which the catheter is inserted into a tortuous blood vessel, the stent 11 is deformed flexibly along the catheter and the stent 11 can be easily delivered to a site of pathology.

Moreover, by configuring so that the stent 11 has the knob portion 19 provided at the apex 17b of the circular body 13, it is possible to suppress the occurrence of metallic fatigue, and thus it is possible to suppress the damage to the stent 11 due to the repetition of diameter reduction and expansion of the stent 11 caused by misplacement and cyclic deformations of the stent 11 caused by a blood flow or a pulsating movement of a blood vessel, etc.

In addition, the flexibility of the stent 11 is improved by multiple and synergistic effects due to the configuration in which the region in which the phase transformation is caused to martensite phase at a deformation portion upon crimping increasing by providing the slit 21 at the apex 17b of the circular body 13, the curve portion 15a of the coiled element 15, and the configuration in which a tangential direction of the curve portion 15a at a connecting end coincides with the longitudinal axis direction LD, and the change in expansive force with respect to the change in the diameter of the stent 11 becomes gentle in the unloading process. As a result of this, the conformability of the stent 11 can be improved and it is also possible to place the stent 11 at a site where the diameter of a blood vessel changes locally such as a tapered blood vessel, without placing an unnecessary load on the blood vessel.

Figure 21:
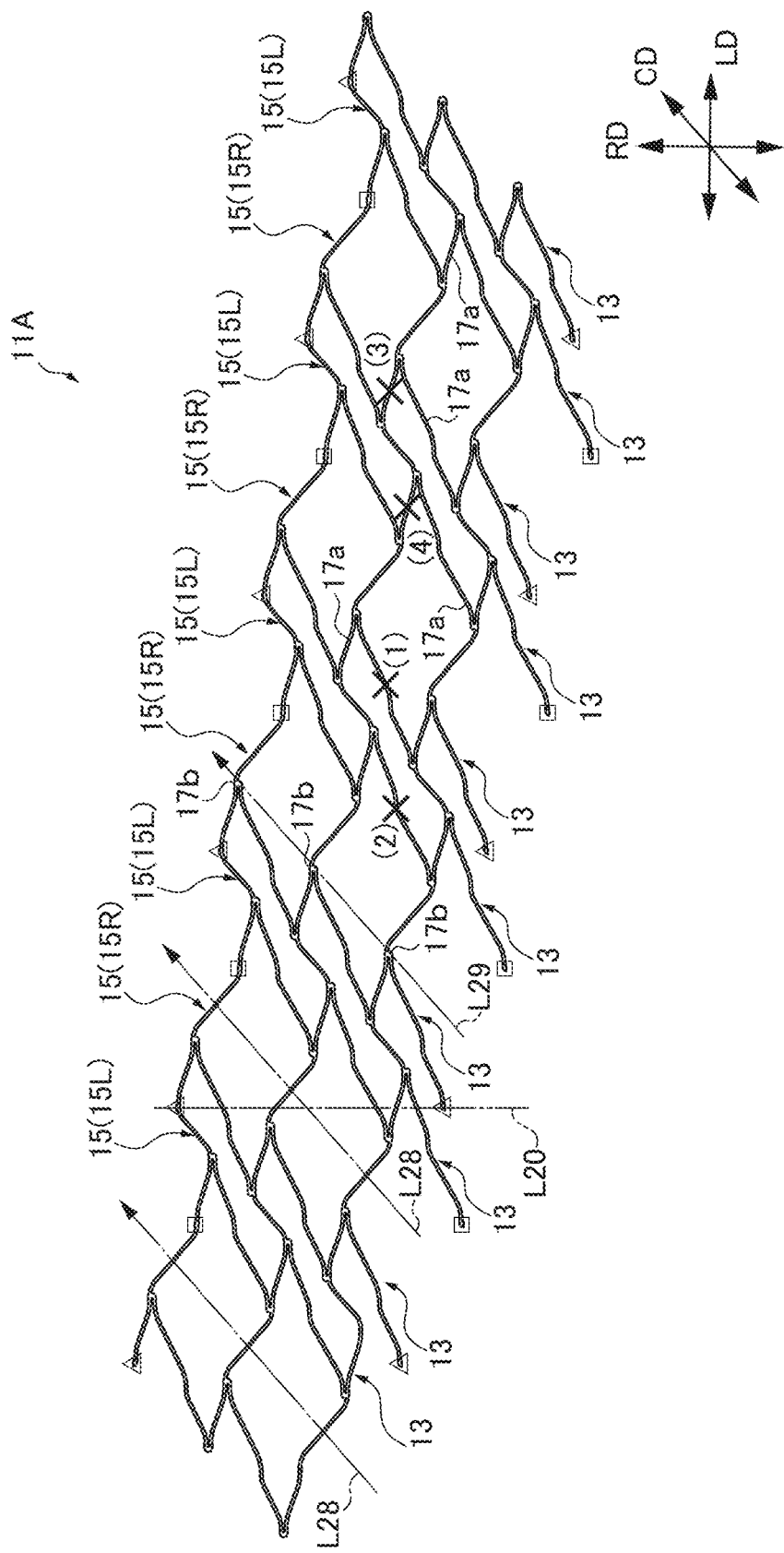
FIG. 21 is a developed view showing the highly flexible stent according to a second embodiment of the present invention to be virtually expanded into a plane.

Next, other embodiments of the present invention are described. For aspects which are not described specifically in the other embodiments, the explanations for the first embodiment are applied as appropriate. Effects similar to the first embodiment are exerted in the other embodiments as well. FIG. 21 is a developed view showing a stent 11A according to a second embodiment of the present invention to be virtually expanded into a plane.

As shown in FIG. 21, the stent 11A according to the second embodiment has substantially the same mesh pattern as the stent 11 according to the first embodiment shown in FIG. 2. In FIG. 21, the symbols Δ (triangle) that overlap in the radial direction RD (refer to a dashed-two dotted line L20 in FIG. 21) or the symbols □ (square) that overlap in the radial direction RD indicate joining points.

The stent 11A according to the second embodiment has a single spiral structure. As shown in FIG. 21, the single spiral structure is a structure in which there is a single spiral L28 between the joining points Δ (triangle) in the reference line L20 extending in the radial direction RD. The wavy-line pattern of a circular body 13 is a zigzagged shape. A virtual line L29 passing through a plurality of apices 17b on the same side of the zigzagged shape is linear.

It should be noted that the stent 11A according to the second embodiment shown in FIG. 21 and the stent 11 according to the first embodiment shown in FIG. 2 are in a mirror image relationship in the axial direction LD. X(1), X(2), X(3), and X(4) in FIG. 21 are used for explaining modified examples described later.

In the stent 11 according to the first embodiment shown in FIG. 2 and the stent 11A according to the second embodiment shown in FIG. 21, the wavy-line pattern body 13 forms a circular body. On the other hand, in the present invention, a wavy-line pattern body 13 can be adopted which is non-continuous in a circumferential direction and does not form a circular body. Compared with the wavy-line pattern body that forms a circular body, the wavy-line pattern body 13 that does not form a circular body has a form in which one or a plurality of struts (leg portions 17a) that constitutes a wavy-line pattern body is omitted. Specific embodiments from a first modified example to a fourth modified example are described in detail below.

Figure 22:
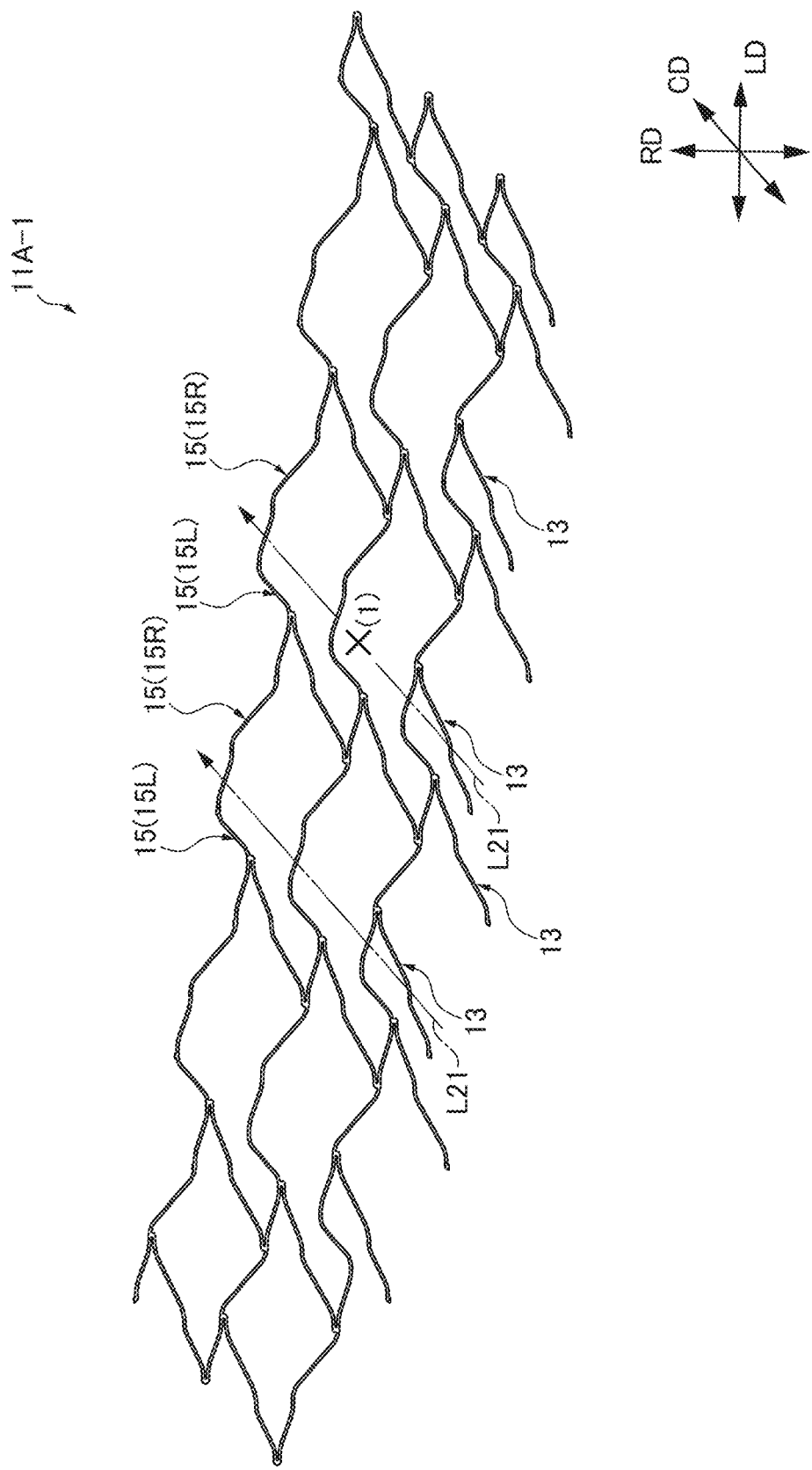
FIG. 22 is a developed view showing the highly flexible stent according to a first modified example of a second embodiment of the present invention to be virtually expanded into a plane.

FIG. 22 is a developed view showing a stent 11A-1 according to a first modified example of the second embodiment of the present invention to be virtually expanded into a plane. The stent 11A-1 of the first modified example has a form in which a plurality of struts including a strut (leg portions 17a) to which X(1) is added in FIG. 21 is omitted. The dashed-two dotted line L21 shows a virtual line along a plurality of struts (leg portions 17a) omitted.

Figure 23:
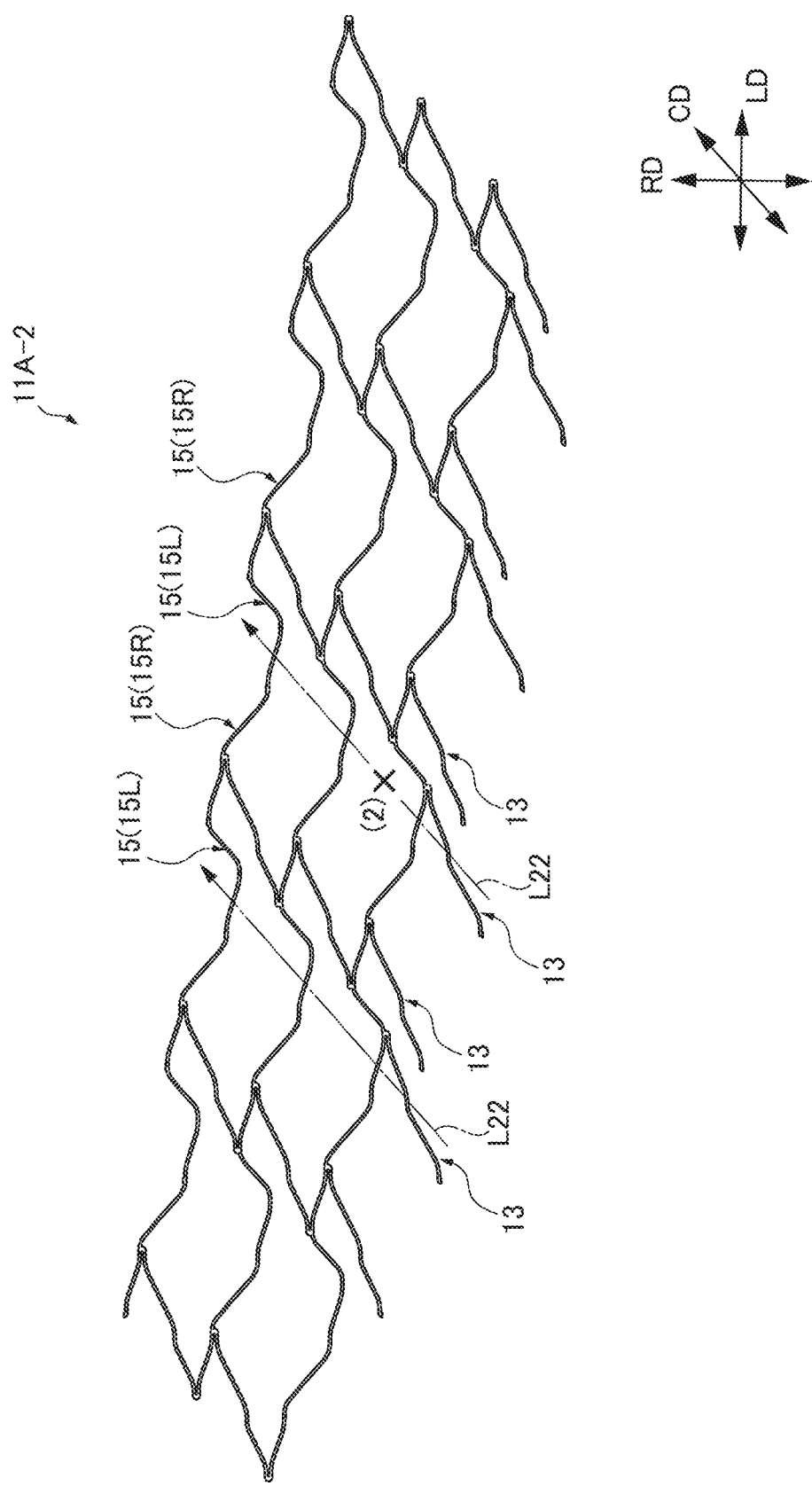
FIG. 23 is a developed view showing the highly flexible stent according to a second modified example of a second embodiment of the present invention to be virtually expanded into a plane.

FIG. 23 is a developed view showing a stent 11A-2 according to a second modified example of the second embodiment of the present invention to be virtually expanded into a plane. The stent 11A-2 of the second modified example has a form in which a plurality of struts including a strut (leg portions 17a) to which X(2) is added in FIG. 21 is omitted. The dashed-two dotted line L22 shows a virtual line along a plurality of struts (leg portions 17a) omitted.

Figure 24:
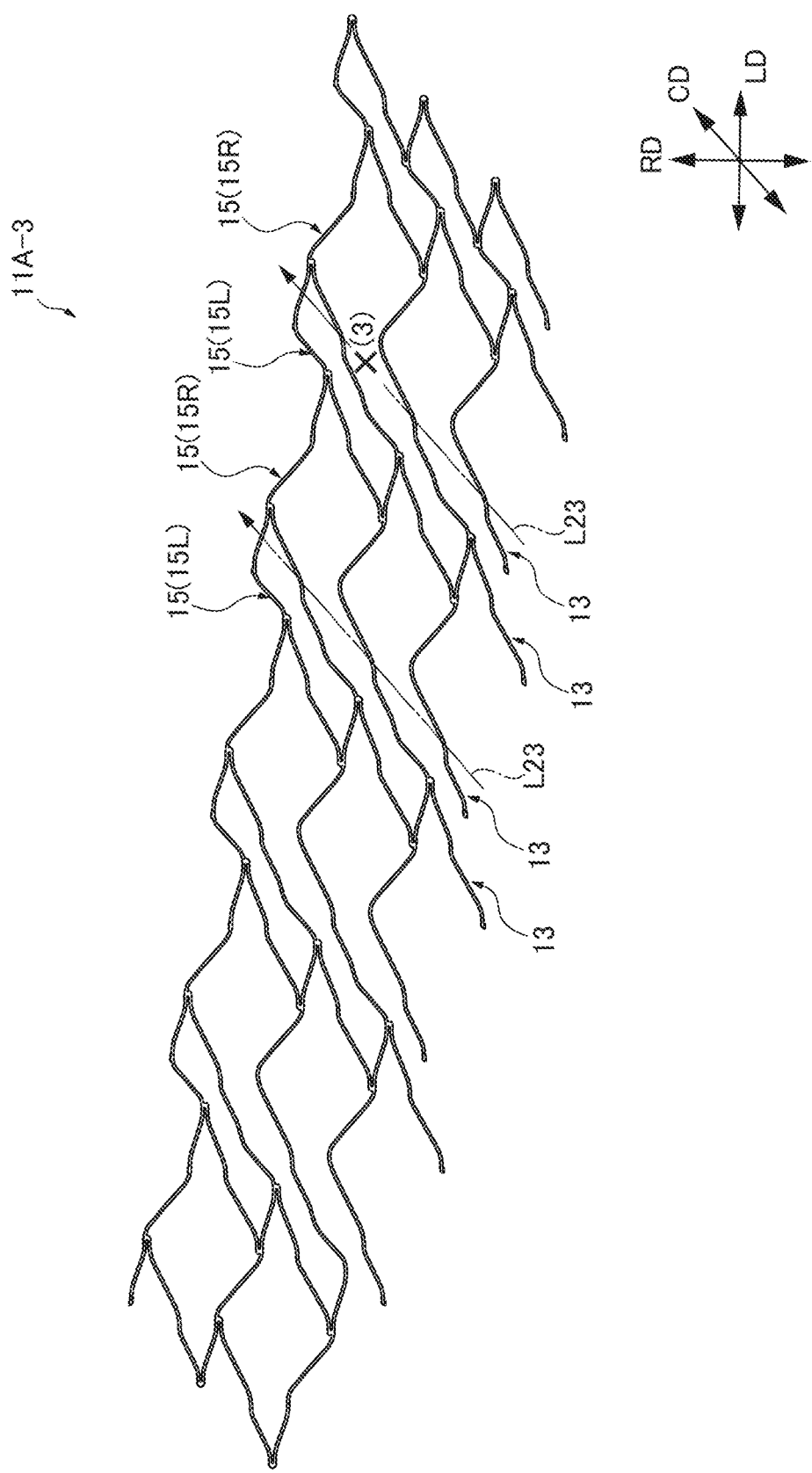
FIG. 24 is a developed view showing the highly flexible stent according to a third modified example of a second embodiment of the present invention to be virtually expanded into a plane.

FIG. 24 is a developed view showing a stent 11A-3 according to a third modified example of the second embodiment of the present invention to be virtually expanded into a plane. The stent 11A-3 of the third modified example has a form in which a plurality of struts including a strut (leg portions 17a) to which X(3) is added in FIG. 21 is omitted. The dashed-two dotted line L23 shows a virtual line along a plurality of struts (leg portions 17a) omitted.

Figure 25:
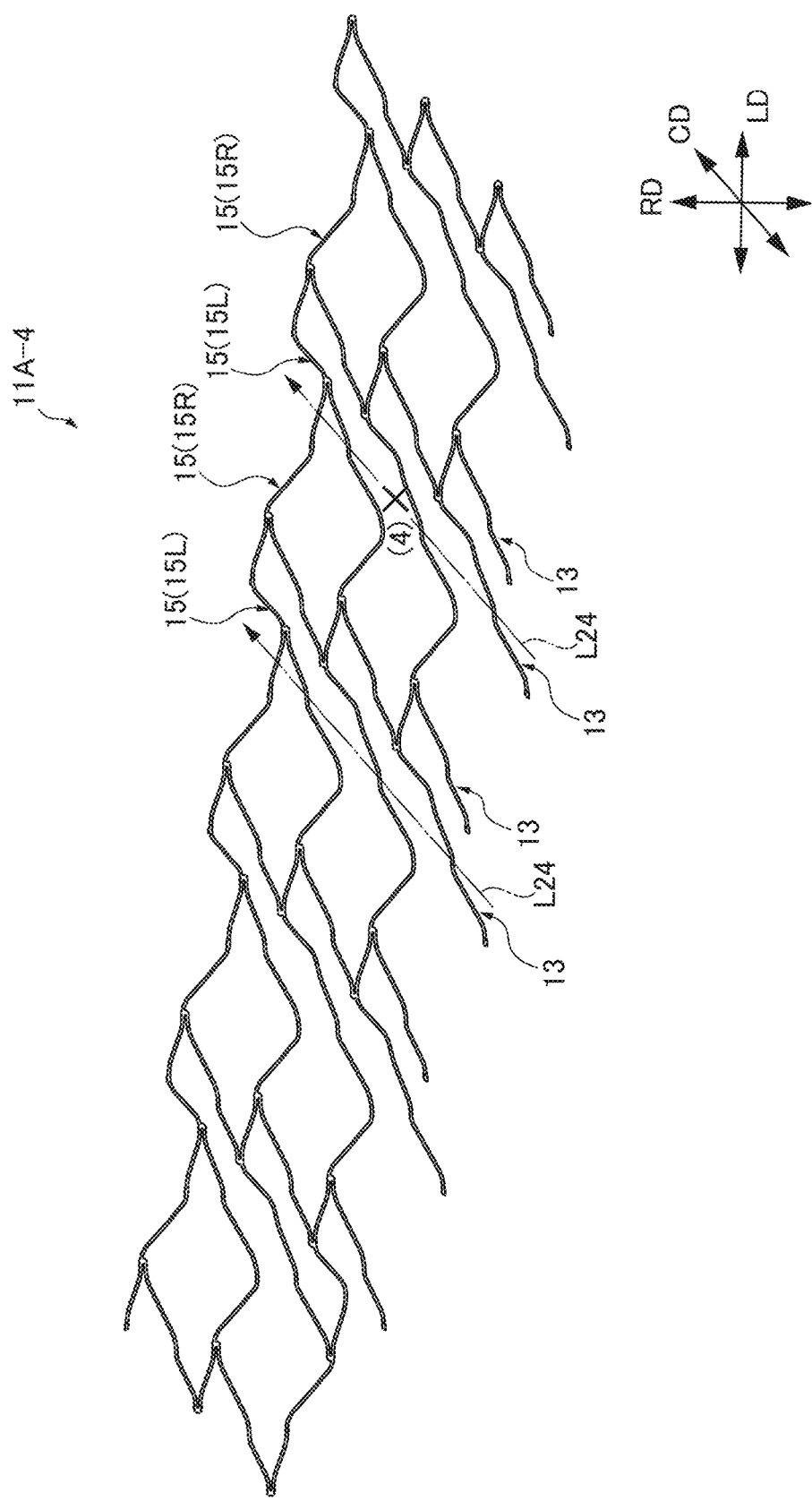
FIG. 25 is a developed view showing the highly flexible stent according to a fourth modified example of a second embodiment of the present invention to be virtually expanded into a plane.

FIG. 25 is a developed view showing a stent 11A-4 according to a fourth modified example of the second embodiment of the present invention to be virtually expanded into a plane. The stent 11A-4 of the fourth modified example has a form in which a plurality of struts including a strut (leg portions 17a) to which X(4) is added in FIG. 21 is omitted. The dashed-two dotted line L24 shows a virtual line along a plurality of struts (leg portions 17a) is omitted.

In the first modified example to the fourth modified example, the number of struts to be omitted can be set as one or a plurality as appropriate in a range in which the shape of the stent 11 can be realized.

Figure 26:
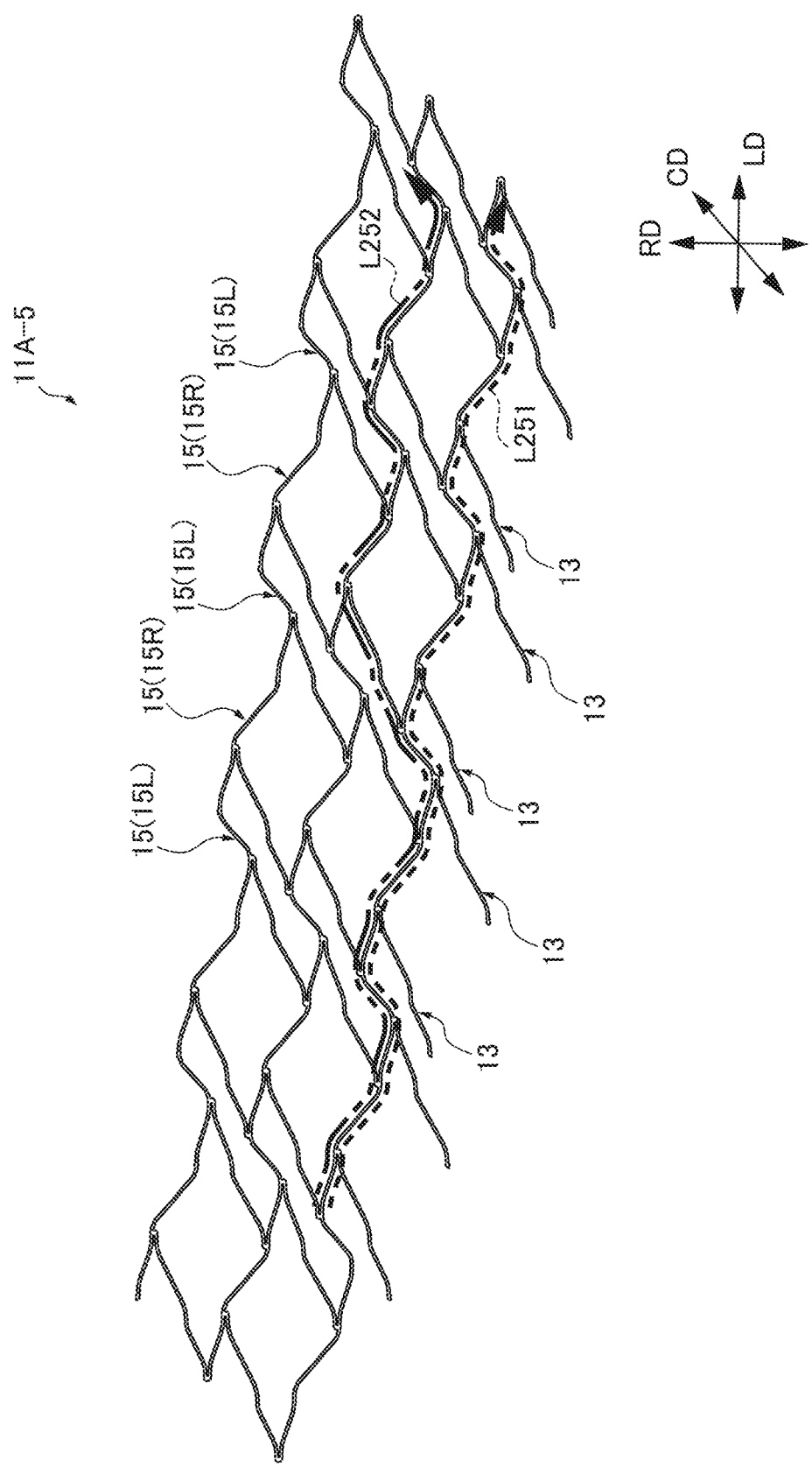
FIG. 26 is a developed view showing the highly flexible stent according to a fifth modified example of a second embodiment of the present invention to be virtually expanded into a plane.

FIG. 26 is a developed view showing a stent 11A-5 according to a fifth modified example of the second embodiment of the present invention to be virtually expanded into a plane. In the stent 11A-5 of the fifth modified example, struts (leg portions 17a of a circular body 13, coiled elements 15) which are continuous in the axial direction LD, becomes thicker than the other struts, a result of which the rigidity of the thick continuous struts becomes higher than the other struts. The thick continuous struts (in FIG. 26, its path is shown by the dashed line L251 or the dashed-two dotted line L252) serve as a backbone. More than one thick continuous strut can be provided to a single stent.

Figure 27:
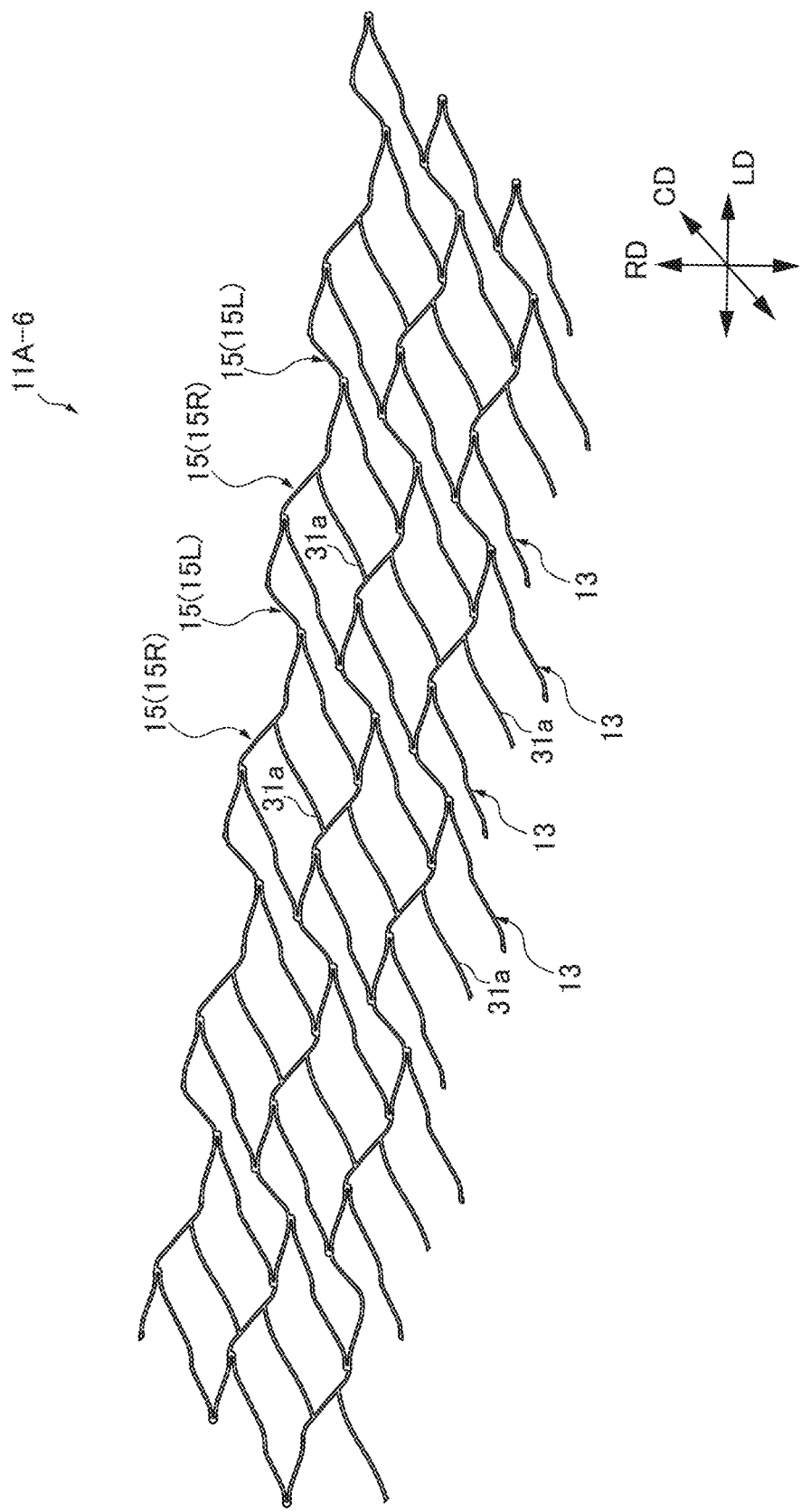
FIG. 27 is a developed view showing the highly flexible stent according to a sixth modified example of a second embodiment of the present invention to be virtually expanded into a plane.

FIG. 27 is a developed view showing a stent 11A-6 according to a sixth modified example of the second embodiment of the present invention to be virtually expanded into a plane. In the stent 11A-6 of the sixth modified example, first additional strut 31a extending in a circular direction CD are provided which connect the coiled elements 15 adjacent in the circular direction CD.

Figure 28:
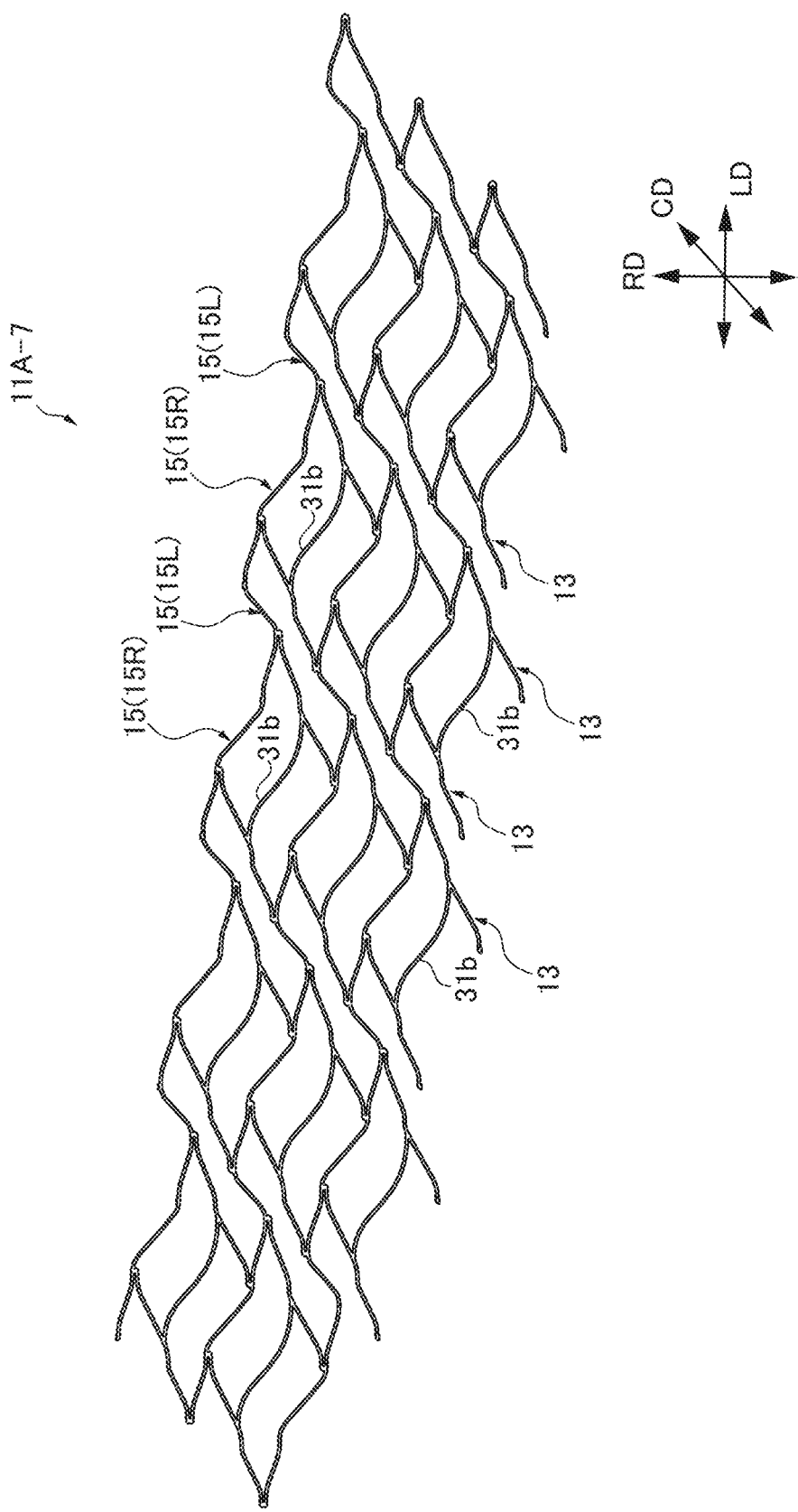
FIG. 28 is a developed view showing the highly flexible stent according to a seventh modified example of a second embodiment of the present invention to be virtually expanded into a plane.

FIG. 28 is a developed view showing a stent 11A-7 according to a seventh modified example of the second embodiment of the present invention to be virtually expanded into a plane. In the stent 11A-7 of the seventh modified example, second additional struts 31b extending in a direction perpendicular to the circular direction CD are provided which connect circular bodies 13 adjacent in a direction perpendicular to the circular direction CD.

It should be noted that the shape of an additional strut, the location of a strut to be provided, the number of struts to be provided, etc., are not limited in particular. Both the first additional strut 31a and the second additional strut 31b may be provided to a single stent 11.

Figure 29:
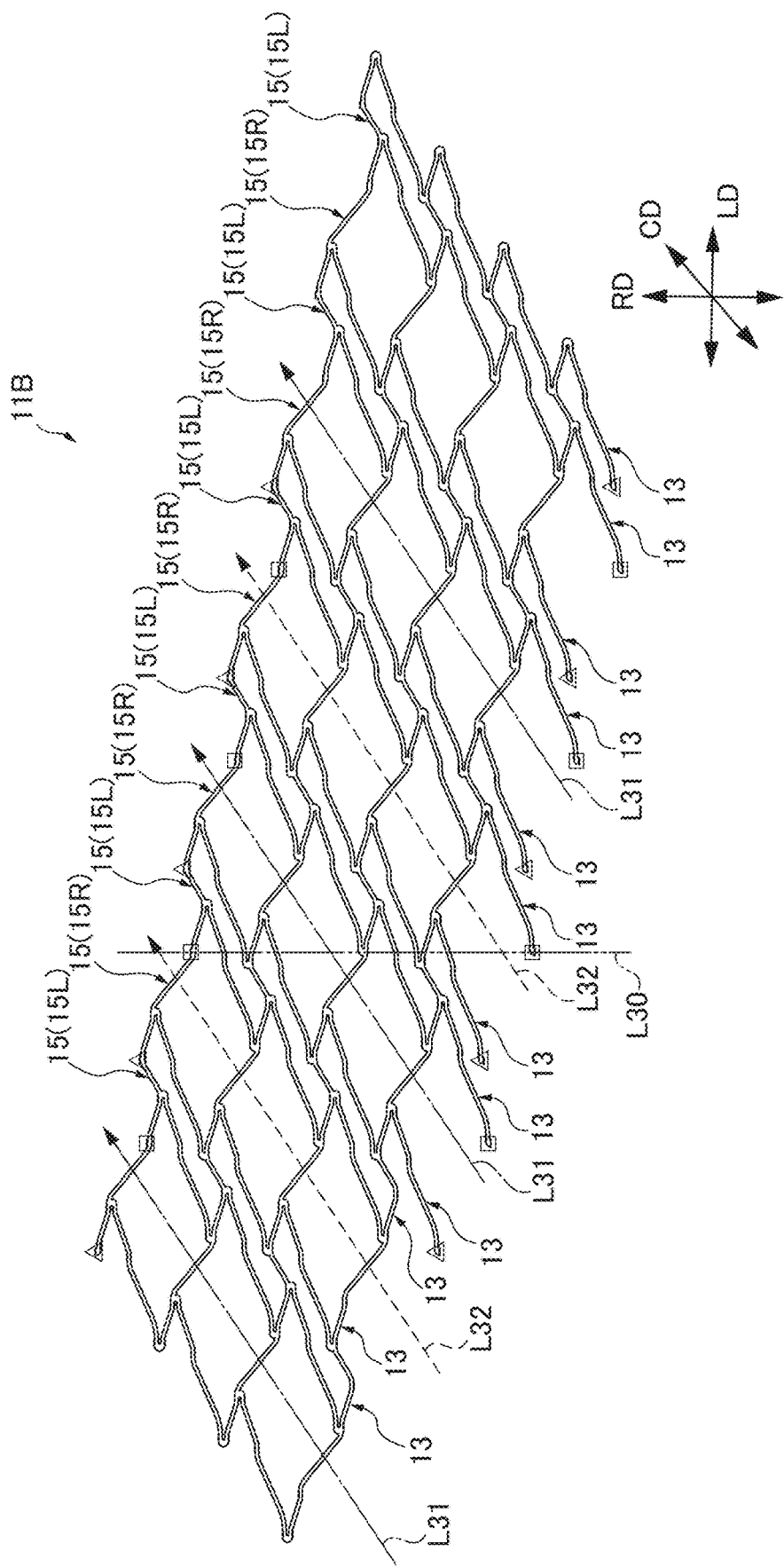
FIG. 29 is a developed view showing the highly flexible stent according to a third embodiment of the present invention to be virtually expanded into a plane.

FIG. 29 is a developed view showing a stent 11B according to a third embodiment of the present invention to be virtually expanded into a plane. The stent 11B according to the third embodiment has a double spiral structure. As shown in FIG. 29, the double spiral structure indicates that there are two spirals of L31 and L32 between joining points □ (square) at a reference line L30 extending in the radial direction RD.

Figure 30:
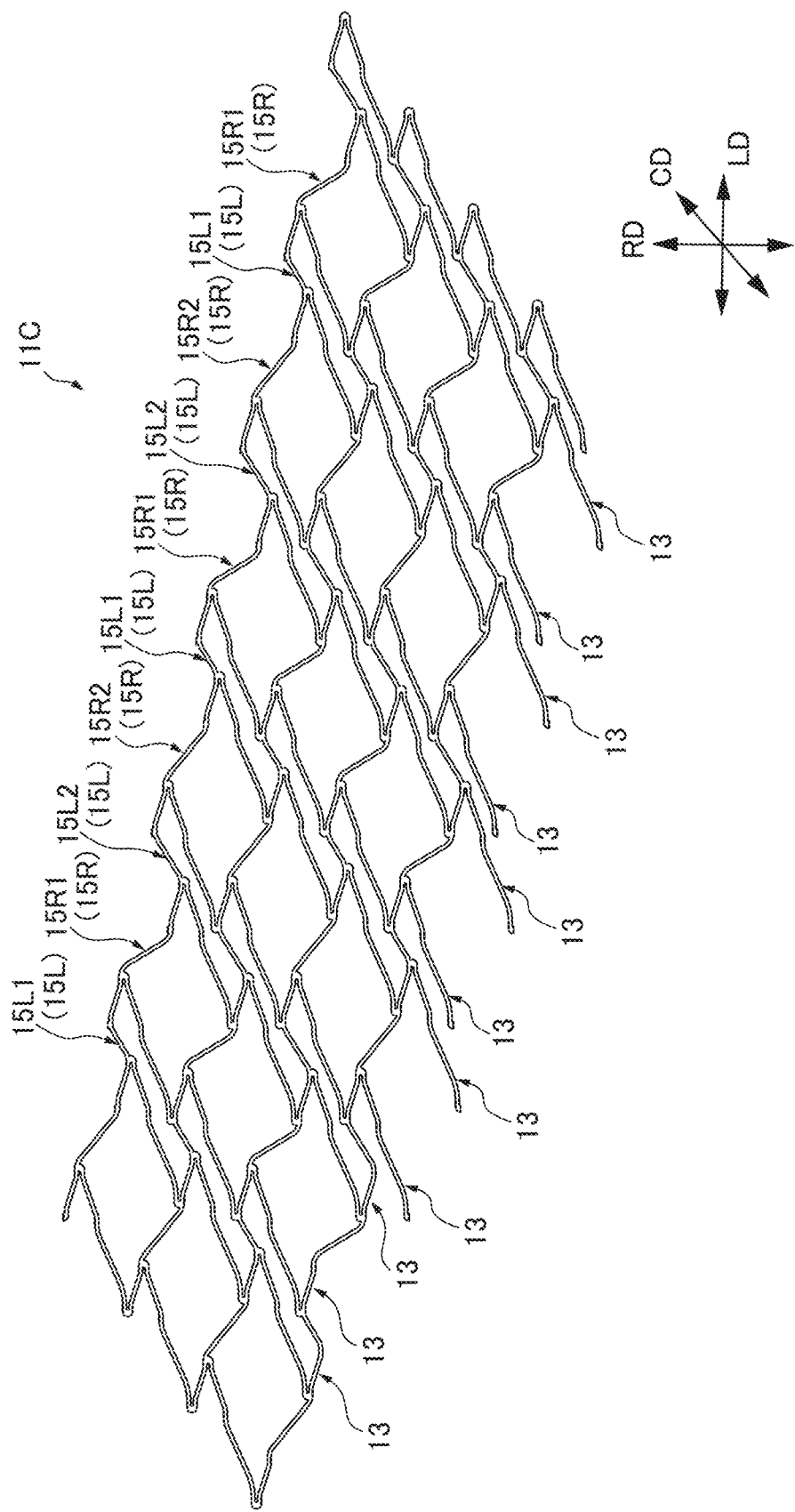
FIG. 30 is a developed view showing the highly flexible stent according to a fourth embodiment of the present invention to be virtually expanded into a plane.

FIG. 30 is a developed view showing a stent 11C according to a fourth embodiment of the present invention to be virtually expanded into a plane.

In the stent 11B according to the third embodiment shown in FIG. 29, one coiled element 15R and the other coiled element 15L are alternately arranged in an axial direction LD. All of the one coiled elements 15R are homomorphic and all of the other coiled elements 15L are homomorphic.

In the stent 11C according to the fourth embodiment shown in FIG. 30, the one coiled element 15R and the other coiled element 15L are alternately arranged in the axial direction LD. When focusing attention on the one coiled elements 15R, one coiled element 15R1 and the other coiled element 15R2 adjacent to each other are heteromorphic. The one coiled elements 15R1 and the other coiled elements 15R2 are alternately arranged. When focusing attention on the other coiled elements 15L, the other coiled element 15L1 and the other coiled element 15L2 adjacent to each other are heteromorphic. The other coiled element 15R1 and the other coiled element 15R2 are alternately arranged.

Figure 31:
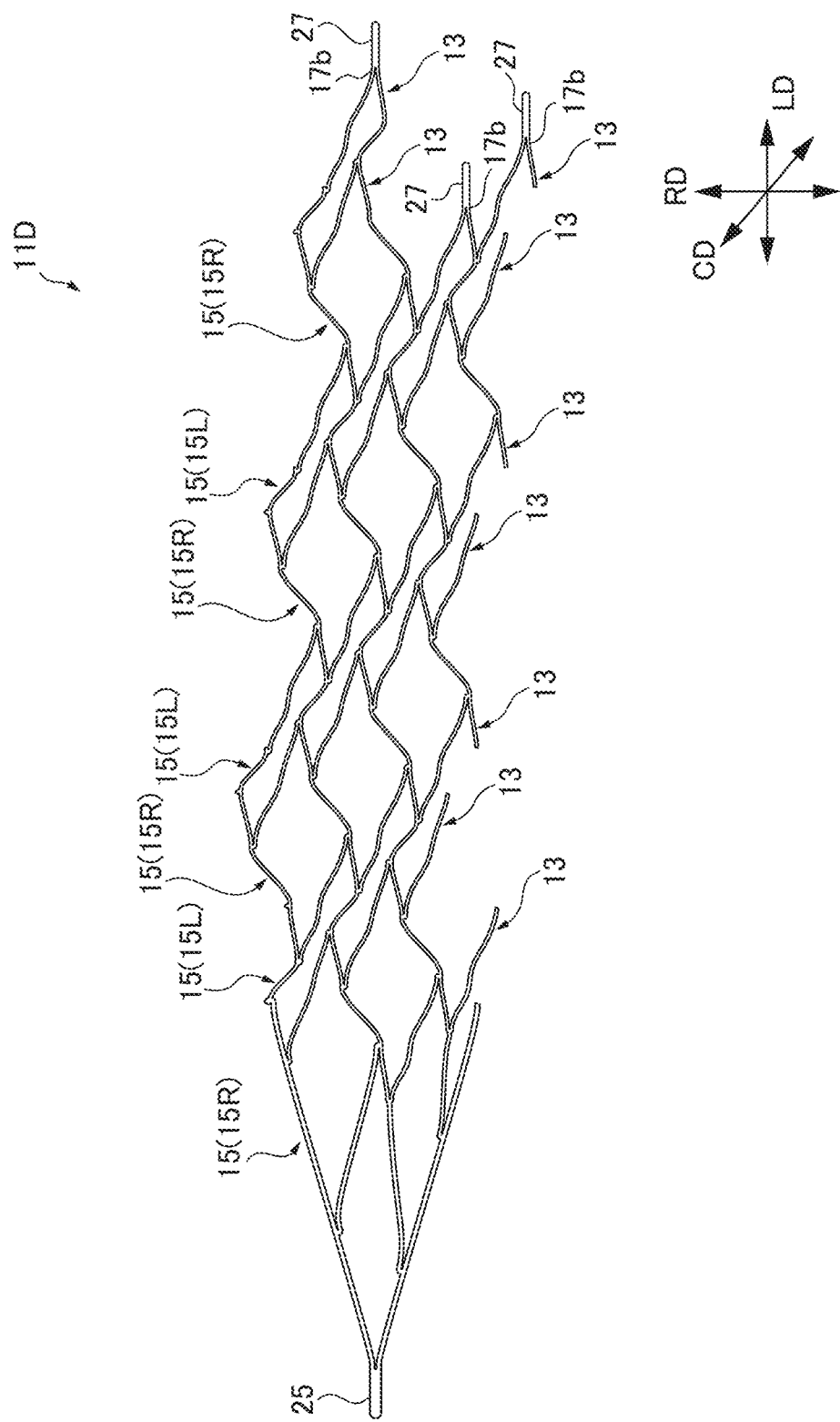
FIG. 31 is a developed view showing the highly flexible stent according to a fifth embodiment of the present invention to be virtually expanded into a plane.
Figure 32A:
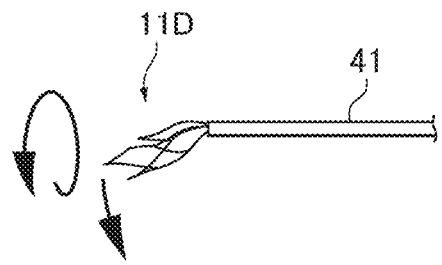
FIGS. 32A, 32B, 32C, and 32D are views showing the behavior of a highly flexible stent of the present invention being pushed out from a catheter and expanded.
Figure 32B:
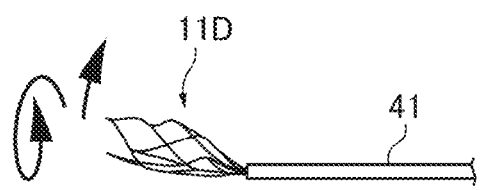
Figure 32C:
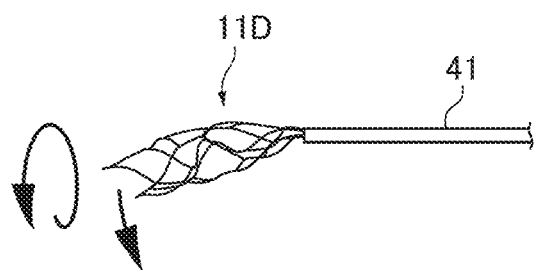
Figure 32D:
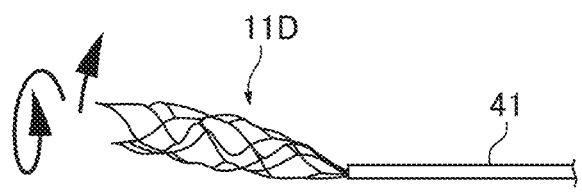

FIG. 31 is a developed view showing a stent 11D according to a fifth embodiment of the present invention to be virtually expanded into a plane. A mesh pattern of the stent 11D according to the fifth embodiment is substantially the same as the mesh pattern of the stent 11A according to the second embodiment shown in FIG. 21. A base end portion 25 side (a side of being connected with a guide wire 51) of the stent 11D according to the fifth embodiment is made narrow in a rod-like shape. In the fifth embodiment, three tip portions 27 (side opposite to the base end portion 25) of the stent 11D are formed in a rod-like shape. The tip portions 27 project in a rod-like shape in the axial direction LD from apices 17b of the circular body 13.

FIGS. 32A to 32D are views showing the behavior of the stent 11D according to the fifth embodiment being pushed out from a catheter 41 and expanded. In practice, the stent 11D is pushed out from a catheter 41 inside a blood vessel and expanded. However, explanations are provided here of the behavior of the stent 11D being pushed out from the catheter 41 in an unconstrained state not inside of a blood vessel and expanded. Since the stent 11D according to the present invention has the abovementioned structure, the stent 11D is pushed out from the catheter 41 in a manner of rotating while swinging and expanded. When the stent 11D having such a behavior is pushed out from the catheter 41 inside of a blood vessel and expanded, the stent 11D cannot be swung. Instead, as shown in FIG. 33, the stent 11D is subject to dig into a blood clot BC that has been trapped.

Figure 33:
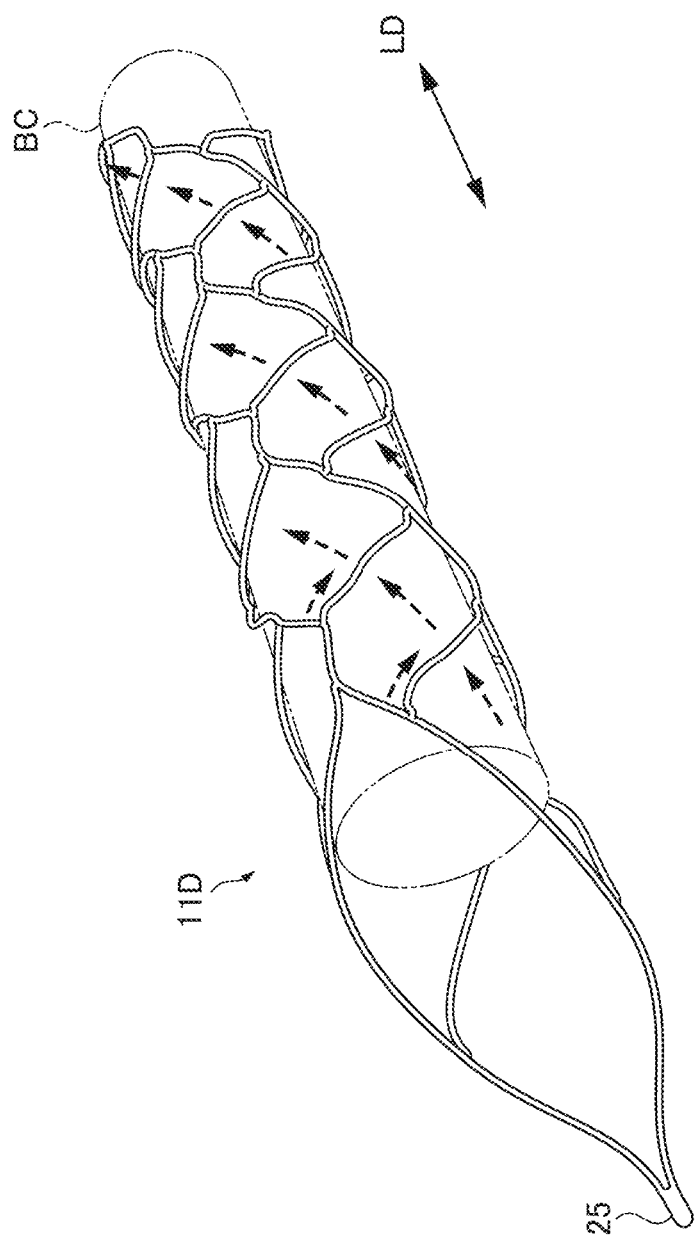
FIG. 33 is a view showing a state in which the highly flexible stent of the present invention traps a blood clot.

Furthermore, as shown in FIG. 33, in a state in which the stent 11D is expanded, a strut is likely to be in a state of expanding in the axial direction LD. With such a configuration, the performance of the stent 11D trapping the blood clot BC (the performance of the stent 11D of digging into blood clot BC) and the conformability of the stent 11D to a blood vessel improve. According to the stent 11D of the present invention, the overall stent 11D can be reduced in diameter, the flexibility during diameter reduction is high, and the durability is also high.

Figure 34:
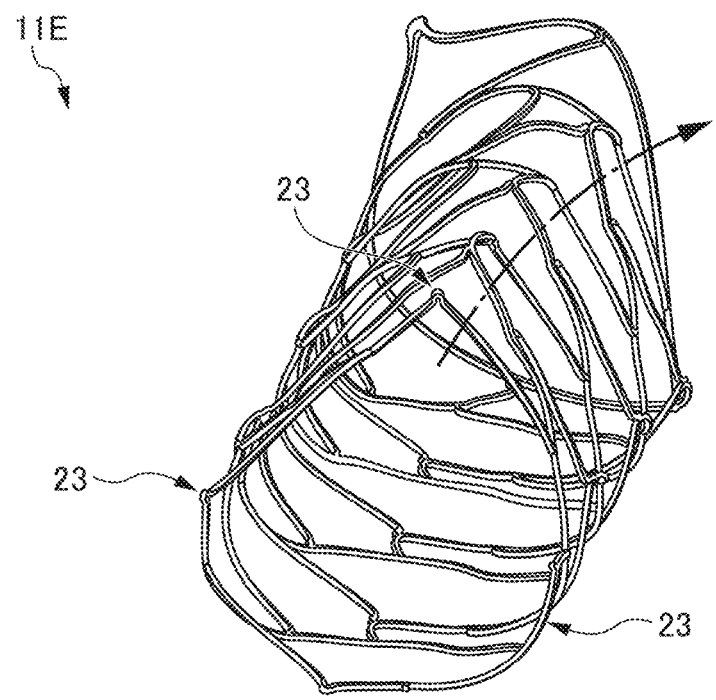
FIG. 34 is a perspective view of a highly flexible stent according to a sixth embodiment of the present invention.
Figure 35:
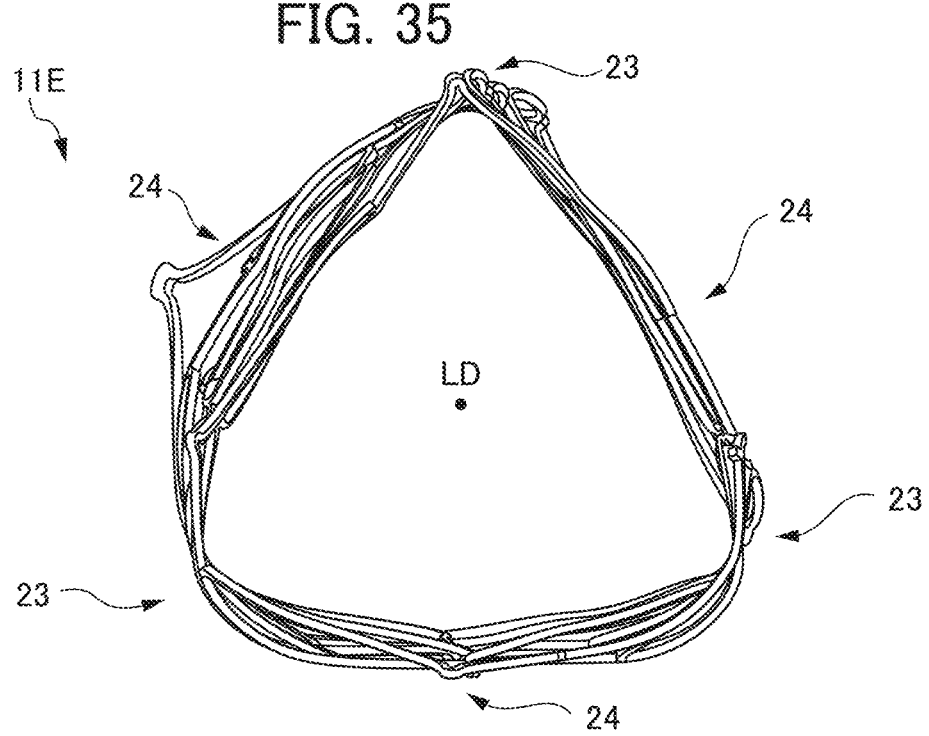
FIG. 35 is a view in which the highly flexible stent shown in FIG. 34 is seen in an axial direction.

Next, a stent 11E according to a sixth embodiment of the present invention is described. FIG. 34 is a perspective view showing the stent 11E according to the sixth embodiment of the present invention. FIG. 35 is a view in which the stent 11E in FIG. 34 is seen in an axial direction. Compared with the first embodiment, the sixth embodiment mainly differs in the cross-sectional shape of the stent.

As shown in FIGS. 34 and 35, the cross sectional shape of the stent 11E according to the sixth embodiment is a substantially triangular shape. Each of the triangle-shape apices 23 is rounded. Each of the triangle-shape apices 23 is aligned in an axial direction LD in such a manner of being spirally displaced in the dashed line direction shown in FIG. 34. It should be noted that each of the triangle-shape apices 23 may be aligned linearly. The substantially triangular shape may be similar forms in the axial direction LD or may not be similar forms. The shape of each side 24 forming the triangular shape may be linear or curved.

The stent 11E having a cross sectional shape of a substantially triangular shape can be obtained as follows, for example. Similarly to the forming method of a stent having a normal cross sectional shape (circular shape, oval shape, and shapes similar thereto), cutout machining is performed by way of laser-machining from a tube. Then, the tube on which the cutout machining was performed is formed to be in a cross section of a substantially triangular shape.

According to the sixth embodiment having a substantially triangular cross sectional shape, it is possible to reduce friction between a blood vessel wall and the stent 11E upon recovery of the stent 11E. Furthermore, by reducing a contact space of the stent 11E with respect to a blood vessel wall, it is possible to reduce friction between a blood vessel wall and the stent 11E upon recovery of the stent 11E.

Figure 36:
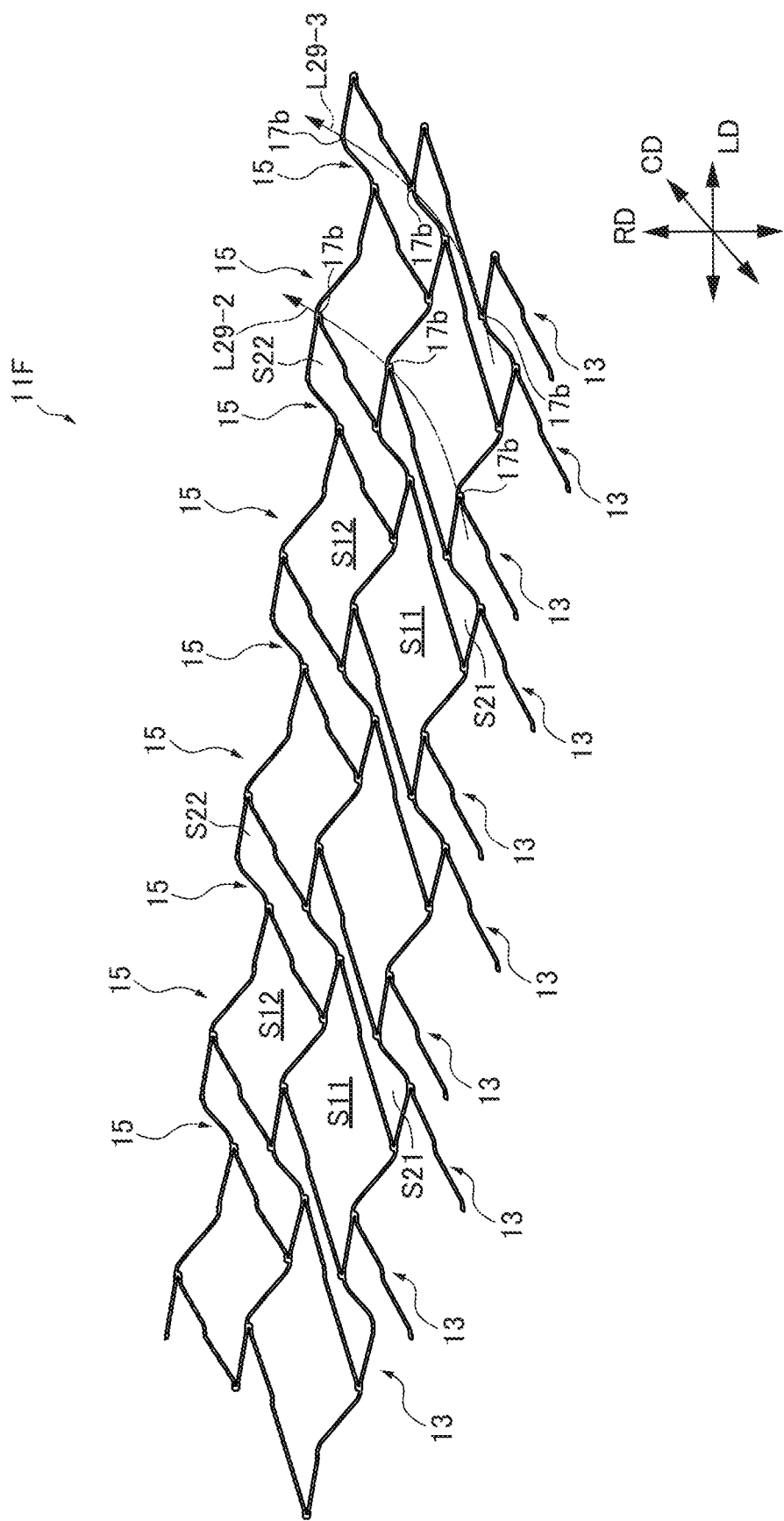
FIG. 36 is a developed view showing that a highly flexible stent according to a seventh embodiment of the present invention is virtually expanded into a plane.

FIG. 36 is a developed view showing a stent 11F according to a seventh embodiment of the present invention to be virtually expanded into a plane. As shown in FIG. 36, virtual lines L29-2 and L29-3 passing through a plurality of apices 17b on the same side of the zigzagged shape of the wavy-line pattern of the circular body 13 are non-linear. The non-linear line includes, for example, a curve having one flexion point (refer to FIG. 36) or a curve having a plurality of flexion points (not shown). In a case of the aspect shown in FIG. 36, the shape of an "area surrounded by struts" Si 1 and the shape of an area S12 adjacent to each other in the circular direction CD differ. Similarly, the shape of an "area surrounded by struts" S21 and the shape of an area S22 adjacent to each other in the circular direction CD differ.

Figure 37:
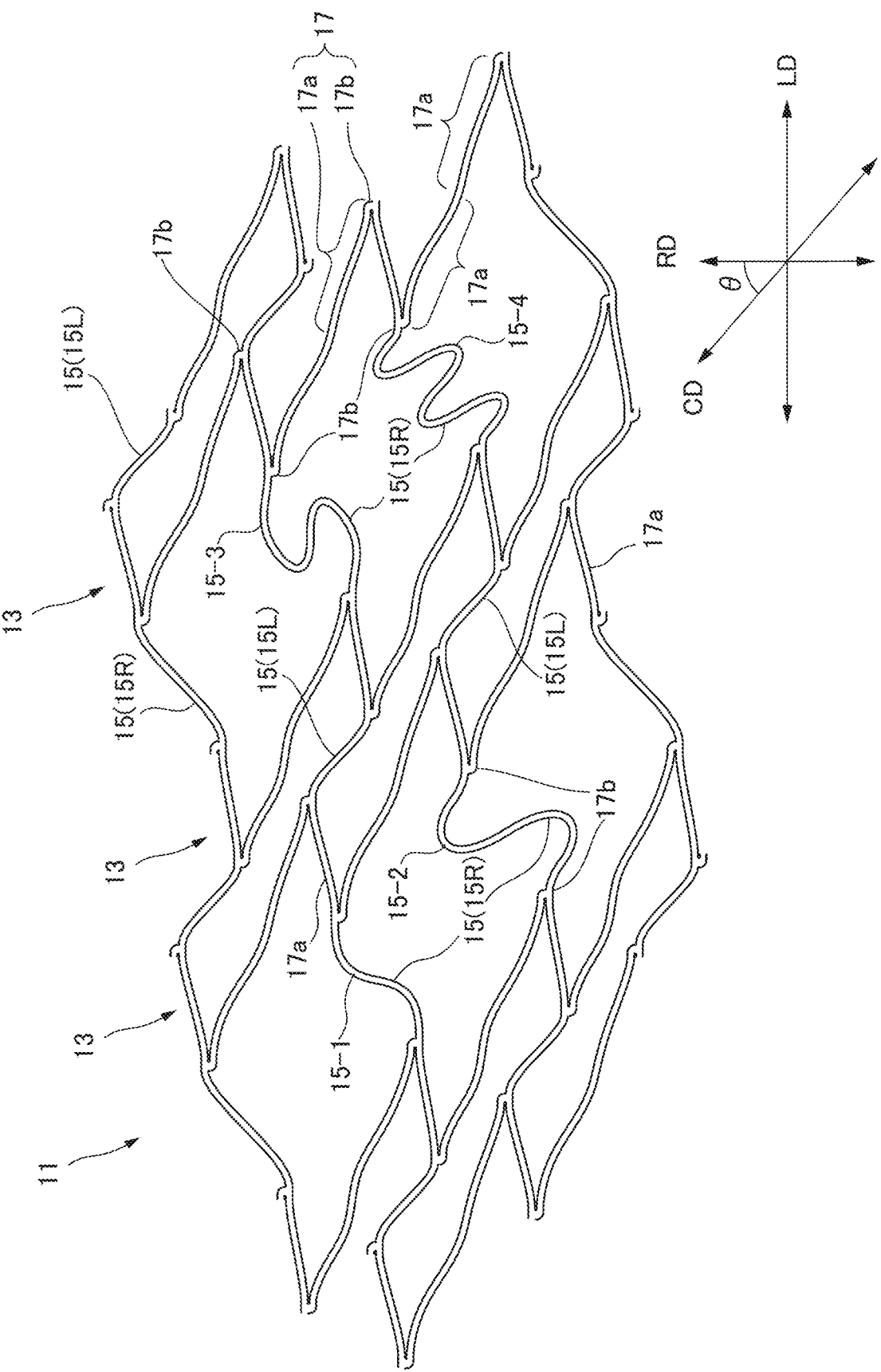
FIG. 37 is a developed view showing various modified examples of a coil element.

FIG. 37 is a developed view showing various modified examples of coiled elements 15. As shown in FIG. 37, a coiled element 15-1 has a greater flexion rate (curvature) than that of the coiled element 15 shown in FIG. 3. A coiled element 15-2 has a greater extent of bending (curvature) than that of the coiled element 15-1. A coiled element 15-3 has a curve which projects in a direction perpendicular to the circular direction CD as well. A coiled element 15-4 has a curve having four flexion points.

Figure 38:
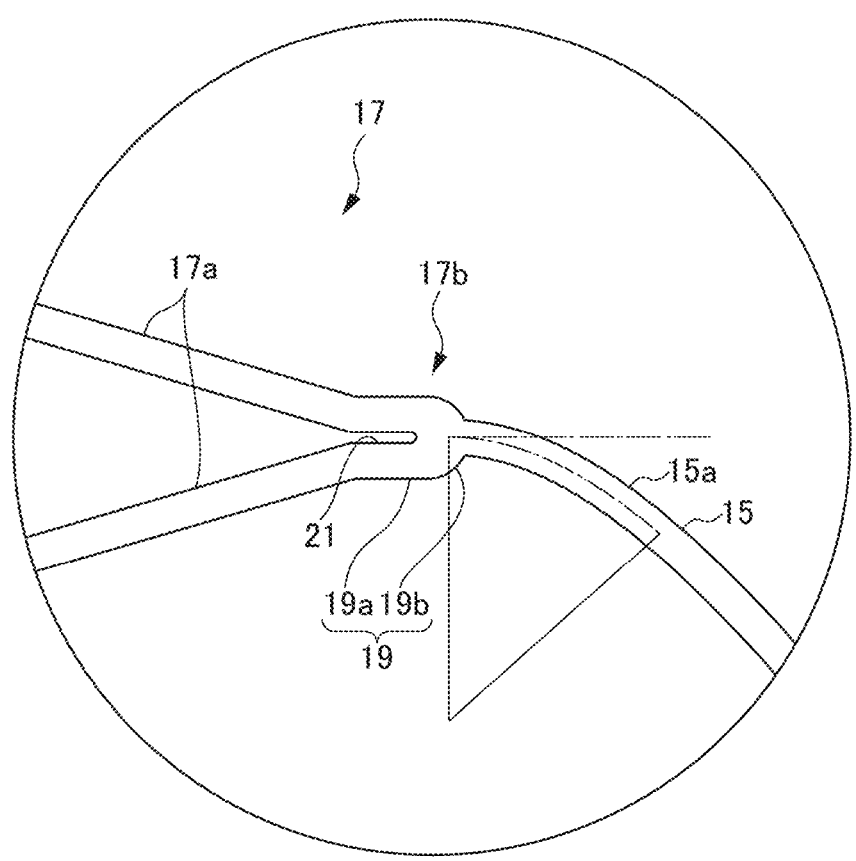
FIG. 38 is a view showing a modified example of a shape of a connecting portion of a coiled element and an apex of a circular body (view corresponding to FIG. 4)

FIG. 38 is a view showing a modified example of the shape of a connecting portion of a coiled element 15 and an apex 17b of a circular body 13 (corresponding to FIG. 4). As shown in FIG. 38, the center in a width direction of an end of the coiled element 15 and an apex (the center in a width direction) of the apex 17b of the circular body 13 match. An end edge in the width direction of the end of the coiled element 15 and an end edge in the width direction of the apex 17b of the circular body 13 are displaced from each other (do not match).

Figure 39:
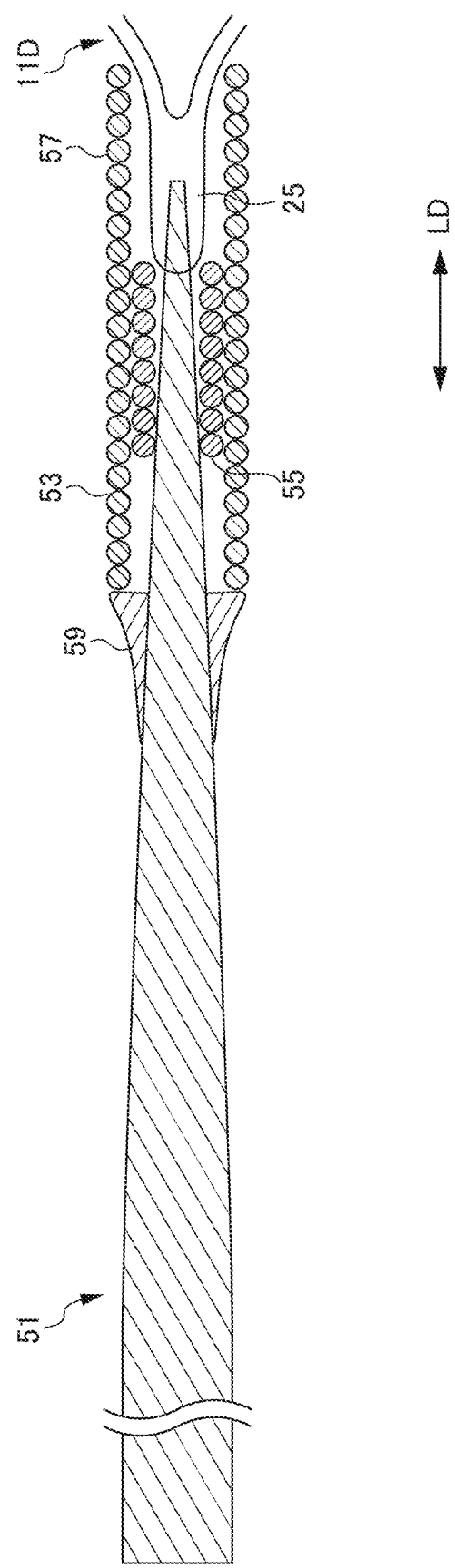
FIG. 39 is a cross sectional view showing a connecting portion of a highly flexible stent of the present invention and a guide wire.

Next, a connecting structure of a highly flexible stent of the present invention and a guide wire is described. FIG. 39 is a cross sectional view showing a connecting portion of the stent 11D of the present invention and a guide wire 51. As shown in FIG. 39, a tip portion 53 of the guide wire 51 is joined with a base end portion 25 of the stent 11D. The tip portion 53 of the guide wire 51 is made narrow to be in a tapered shape. Inner coiled springs 55 are extrapolated at an area adjacent to the base end portion 25 of the stent 11D at the tip portion 53 of the guide wire 51.

Outer coiled springs 57 are extrapolated across the base end portion 25 of the stent 11D, the inner coiled springs 55, and an area adjacent to the inner coiled springs 55 at the tip portion 53 of the guide wire 51. In other words, a double spring composed of the inner coiled springs 55 and the outer coiled springs 57 is provided. Regarding one end portion of the outer coiled springs 57, its movement in the axial direction LD is restricted due to an expanded portion of the stent 11D. Regarding the other end portion of the outer coiled springs 57, its movement in the axial direction LD is restricted due to a welded portion 59 which becomes thick at an outer circumference of the tip portion 53 of the guide wire 51 being joined with the tip portion 53 of the guide wire 51.

Figure 40:
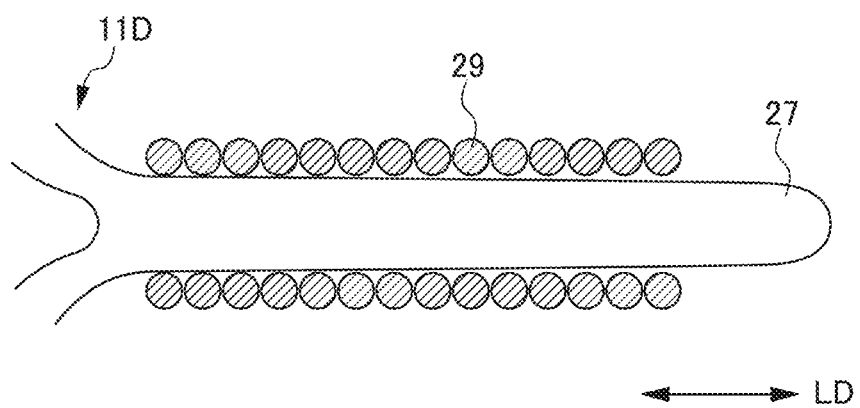
FIG. 40 is a cross sectional view showing a tip portion of a highly flexible stent of the present invention.

FIG. 40 is a cross sectional view showing the tip portion 27 of the stent 11D of the present invention. Coiled springs 29 are extrapolated at the rod-like tip portion 27. A tip end of the tip portion 27 protrudes from the coiled springs 29.

Materials for each coiled spring are described. The material for the outer coiled springs 57 is not specifically limited so far as being a material that can form a coil, and includes, for example, stainless steel (SUS). Materials for the inner coiled springs 55 and the coiled springs 29 are preferably materials that are radio-opaque and can form a coil. With such materials, the inner coiled springs 55 and the coiled springs 29 serve as a marker that is a mark upon surgery. These materials include platinum-iridium (Pt—Ir) alloy.

The joining method of the coiled springs 29 and the tip portion 27 of the stent 11D is not specifically limited so far as being a joining method used for a medical device such as welding, UV adhesion and infiltration of silver solder.

The welding method includes, for example, a method of adhesively fixing by melting the coiled springs 29 and the tip portion 27 of the stent 11D, and a method of melting an area that projects from the coiled springs 29 at the tip portion 27 of the stent 11D thereby restricting the movement of the coiled springs 29.

In the case of UV adhesion, the coiled springs 29 are fixed at the tip portion 27 of the stent 11D using radiation curing polymer of medical grade. The procedure includes: applying liquid curing polymer to the tip portion 27 of the stent 11D; and after the coiled springs 29 are placed thereon, promoting the curing of the liquid curing polymer by applying radiation thereto, thereby fixing the coiled springs 29 to the tip portion 27 of the stent 11D.

In the case of infiltration of silver solder, the coiled springs 29 are formed from a material different from that of the stent 11D, and silver solder, etc. is infiltrated to the coiled springs 29 from above, thereby fixing the coiled springs 29 to the tip portion 27 of the stent 11D.

Although the stents according to the present invention are described with reference to the illustrated embodiments, the present invention is not limited to the illustrated embodiments. For example, the length of the one coiled element 15R may be equivalent to the length of the other coiled element 15L. Both the length of the one coiled element 15R and the length of the other coiled element 15L may be longer than the length of the leg portion 17a or shorter than the length of the leg portion 17a. The spiral direction of the coiled element 15 may be right-handed or left-handed.

The invention claimed is:

1. A method for capturing a thrombus with a catheter and a stent which is inserted in and pushed out of the catheter, the stent being configured to be pushed out of the catheter to unfold while rotating and swinging when the stent is pushed out of the catheter in a state of being unrestrained, the method comprising:
pushing the stent out of the catheter inside a blood vessel; and
capturing a thrombus,
wherein the stent includes:
a plurality of first bodies of a first pattern, each first body having a first element, an adjacent pair of the first bodies being arranged so as to share only a part of the first element thereof; and
a plurality of second bodies of a second pattern interconnected with the first bodies, each second body having a second element, an adjacent pair of the second bodies being arranged so as to share only a part of the second element thereof,
wherein each of the plurality of first bodies is configured to share a common part with at least one of the plurality of second bodies so as to be adjacent to each other,
wherein the first bodies and the second bodies are respectively arranged in a circular direction that is inclined by an inclination with respect to a circumferential direction perpendicular to a direction of a longitudinal axis of the stent in a deployed state of the stent, thereby the first element of the first bodies and the second element of the second bodies are wound about the longitudinal axis of the stent in a spiral manner in a tubular state of the stent, and wherein a winding direction of the first element is opposite to a winding direction of the second element with respect to the longitudinal axis of the stent, such that a deformation in a radial direction due to a distortion load is suppressed.

2. The method according to claim 1, wherein an apex of each first body and an apex of each second body are connected with each other by way of the first element or the second element.

* * * * *